(12) United States Patent
Comando

(10) Patent No.: US 11,860,140 B2
(45) Date of Patent: *Jan. 2, 2024

(54) DETERMINATION OF CONCENTRATIONS AND AMOUNTS OF PERFLUOROALKYL SUBSTANCES BY LC/MS/MS

(71) Applicant: Suffolk County Water Authority, Oakdale, NY (US)

(72) Inventor: Amanda Comando, Smithtown, NY (US)

(73) Assignee: SUFFOLK COUNTY WATER AUTHORITY, Oakdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/662,780

(22) Filed: May 10, 2022

(65) Prior Publication Data
US 2022/0276209 A1 Sep. 1, 2022

Related U.S. Application Data

(63) Continuation of application No. 16/708,812, filed on Dec. 10, 2019, now Pat. No. 11,360,060.

(51) Int. Cl.
*G01N 30/72* (2006.01)
*G01N 30/16* (2006.01)

(52) U.S. Cl.
CPC ......... *G01N 30/7233* (2013.01); *G01N 30/16* (2013.01)

(58) Field of Classification Search
CPC ............................ G01N 30/7233; G01N 30/16
USPC ........................................................ 73/61.55
See application file for complete search history.

(56) References Cited

U.S. PATENT DOCUMENTS

| 10,593,527 | B1 | 3/2020 | Comando |
| 10,872,752 | B2 | 12/2020 | Comando |
| 11,360,060 | B2 * | 6/2022 | Comando .......... G01N 30/7233 |
| 2009/0294660 | A1 | 12/2009 | Whitehouse et al. |
| 2021/0118657 | A1 | 4/2021 | Comando |
| 2021/0172915 | A1 | 6/2021 | Comando |

OTHER PUBLICATIONS

Huset et al., "Quantitative Determination of Perfluoroalkyl Substanace (PFAS) in Soil, Water, and Home Garden Produce", MethodsX, Elsevier, pp. 697-704. 2018.

* cited by examiner

*Primary Examiner* — John Fitzgerald
*Assistant Examiner* — Rodney T Frank
(74) *Attorney, Agent, or Firm* — Heslin Rothenberg Farley & Mesiti P.C.; Nicholas Mesiti

(57) ABSTRACT

A method and system for injecting an unconcentrated sample into a receiving LC/MS/MS system that is configured to determine a concentration of one or more PFAS analytes within the unconcentrated sample, wherein the LC/MS/MS includes ESI. The unconcentrated sample may be subjected to one or more of the following ESI conditions: i) a probe gas temperature of approximately 120° C. to approximately 180° C.; ii) a sheath gas heater setting of approximately 250° C. to approximately 400° C.; and/or iii) a sheath gas flow of approximately 8 L/min to approximately 12 L/min. The unconcentrated sample's concentration and/or an injected amount of the one or more PFAS analytes is determined.

22 Claims, 2 Drawing Sheets

DETERMINATION OF CONCENTRATIONS AND AMOUNTS OF PERFLUOROALKYL SUBSTANCES BY LC/MS/MS

CROSS-REFERENCE TO RELATED APPLICATION

This application is a continuation of U.S. patent application Ser. No. 16/708,812 filed on Dec. 10, 2019. The entire disclosure of the prior application is hereby incorporated herein by reference in its entirety.

FIELD OF THE INVENTION

Embodiments of the present invention relate to qualitative and quantitative analysis of analytes in samples and more particularly to the qualitative and quantitative analysis of perfluoroalkyl substances in water.

BACKGROUND

Per- and polyfluoroalkyl substances (PFAS) are a group of man-made chemicals that includes perfluorooctanoic acid along with its conjugate base perfluorooctanoate (PFOA) and perfluorooctanesulfonic acid along with its conjugate base perfluorooctanesulfonate (PFOS), as well as many other chemicals. PFAS have been manufactured and used in a variety of industries around the globe since the 1940s. In general, PFAS are not readily degraded by natural means, e.g., metabolism, due to their highly fluorinated structures. Thus, PFAS accumulate over time in nature as well as in living tissues. There is evidence that exposure to PFAS can lead to adverse human health effects.

Because of their widespread industrial usage, PFOA and PFOS are the most studied PFAS. Studies indicate that PFOA and PFOS can cause reproductive and developmental, liver and kidney, and immunological effects in laboratory animals. Both chemicals have caused tumors in animals. The most consistent findings are increased cholesterol levels among exposed populations. PFOA and PFOS exposure has been attributed to low infant birth weights, effects on the immune system, cancer (for PFOA), and thyroid hormone disruption (for PFOS).

Recently, PFOA has been detected in the Hoosic River near Hoosick Falls, NY, presumably originating from a plant upstream from Hoosick Falls. Events such as this have triggered significant interest in finding inexpensive and sensitive methods for detecting PFAS such as PFOA and PFOS in other public water sources that are near plants that produce PFAS.

SUMMARY OF INVENTION

Shortcomings of the prior art are overcome and additional advantages are provided through the provision of methods and a system for detecting PFAS analytes and a PFAS analyte detection system for detecting one or more PFAS analytes of formula CnF(2n+1)—X in a solution and/or an unconcentrated sample, wherein n is 3, 4, 5, 6, 7, 8 or 9, and wherein —X is —SO3H, —CO2H, —SO3-, or —CO2—.

In a first aspect, a method is provided for facilitating detecting PFAS analytes that comprises injecting a solution and/or unconcentrated sample into a receiving LC/MS/MS (liquid chromatography/tandem mass spectroscopy) system, which is configured to determine concentrations of one or more PFAS analytes of formula CnF(2n+1)—X within the solution and/or unconcentrated sample, wherein the LC/MS/MS includes electrospray ionization (ESI); subjecting the solution and/or unconcentrated sample to the following ESI conditions: i) a probe gas temperature of approximately 120° C. to approximately 180° C., ii) a sheath gas heater setting of approximately 250° C. to approximately 400° C., and iii) a sheath gas flow of approximately 8 L/min to approximately 12 L/min; and determining one or both of: i) a concentration of at least one of the one or more PFAS analytes within the unconcentrated sample, wherein the concentration of the at least one PFAS analyte is between approximately 0.0020 µg/L and approximately 0.25 µg/L; and ii) an amount of at least one of the one or more PFAS analytes within the injected volume of the unconcentrated sample, wherein the amount of the at least one PFAS analyte is between approximately $1.5 \times 10^{-7}$ µg and approximately $1.9 \times 10^{-5}$ µg.

In a second aspect, a PFAS analyte detection system is provided for that comprises an LC/MS/MS system operable utilizing ESI and configured to: receive an injected volume of the solution and/or unconcentrated sample; subject the injected volume of the unconcentrated sample to ESI conditions as follows: i) a probe gas temperature of approximately 120° C. to approximately 180° C., ii) a sheath gas heater setting of approximately 250° C. to approximately 400° C., and iii) a sheath gas flow of approximately 8 L/min to approximately 12 L/min; and determine one or both of: i) a concentrations of at least one of the one or more PFAS analytes within the unconcentrated sample, wherein the concentration of the at least one PFAS analyte is between approximately 0.0020 µg/L and approximately 0.25 µg/L and ii) an amount of at least one of the one or more PFAS analytes within the injected volume of the unconcentrated sample, wherein the amount of the at least one PFAS analyte is between approximately $1.5 \times 10^{-7}$ µg and approximately 1.9×jig.

In a third aspect, a method is provided for facilitating detecting PFAS analytes that comprises:

obtaining an unconcentrated sample containing one or more PFAS analytes of formula CnF(2n+1)—X as described above;

receiving data representative of test results of an analysis of a concentration and/or amount of at least one of the one or more PFAS analytes of formula CnF($2n$+1)—X within at least a portion of the unconcentrated sample, wherein the test results comprising one or both:

i) the concentration of the at least one PFAS analyte in the unconcentrated sample; and
ii) the amount within an injected volume of the unconcentrated sample of the at least one PFAS analyte into an LC/MS/MS system; and wherein the analysis comprised the following steps a) and b):
a) injecting a volume of the unconcentrated sample into the LC/MS/MS system with ESI that is configured to determine the concentration of the at least one PFAS analyte; and
b) subjecting the injected volume of the unconcentrated sample to ESI conditions as follows:
i) a probe gas temperature of approximately 120° C. to approximately 180° C.;
ii) a sheath gas heater setting of approximately 250° C. to approximately 400° C.; and
iii) a sheath gas flow of approximately 8 L/min to approximately 12 L/min.

In an embodiment, the method and systems further comprises: i) the concentration of the at least one PFAS analyte within the solution and/or unconcentrated sample is between approximately 0.010 µg/L and approximately 0.25 µg/L;

and/or ii) the amount of the at least one PFAS analyte within the injected volume of the unconcentrated sample is between approximately $7.5 \times 10^{-7}$ µg and approximately $1.9 \times 10^{-5}$ µLg.

In an embodiment, the method and systems further comprises subjecting the solution and/or unconcentrated sample to the following ESI conditions: i) a gas flow setting of between approximately 11 L/min to approximately 20 L/min; and ii) a capillary voltage setting of between approximately 1500 V to approximately 4000 V.

In an embodiment, the method and systems further comprises subjecting the solution and/or unconcentrated sample to the following ESI conditions: i) a gas flow setting of between approximately 11 L/min to approximately 20 L/min; and ii) a capillary voltage setting of between approximately 1500 V to approximately 4000 V.

In an embodiment, the method and systems further comprises subjecting the solution and/or unconcentrated sample to the following ESI conditions: i) a probe gas temperature of approximately 120° C.; ii) a sheath gas heater setting of approximately 400° C.; and iii) a sheath gas flow of approximately 8 L/min.

In an embodiment, the method and systems further comprises subjecting the solution and/or unconcentrated sample to the following ESI conditions: i) a gas flow setting of approximately 11 L/min; and ii) a capillary voltage setting of approximately 1500 V.

In an embodiment, the method and systems further comprises the one or more PFAS analytes of formula $C_nF_{(2n+1)}$—X are chosen from: PFBA, PFBS, PFDA, PFHpA, PFHpS, PFHxA, PFHxS, PFNA, PFPeS, PFOA, and PFOS.

In an embodiment, the unconcentrated sample and/or solution are aqueous unconcentrated samples and/or solutions. In this embodiment, the aqueous unconcentrated samples and/or solutions are selected from: finished drinking water, ground water, raw source water, and water at an intermediate stage of treatment between raw source water and finished drinking water. Further, the unconcentrated sample and/or solution may contain analytes other than PFAS such as impurities from the water source, preservatives, buffers, etc.

DETAILED DESCRIPTION

Figure 1:
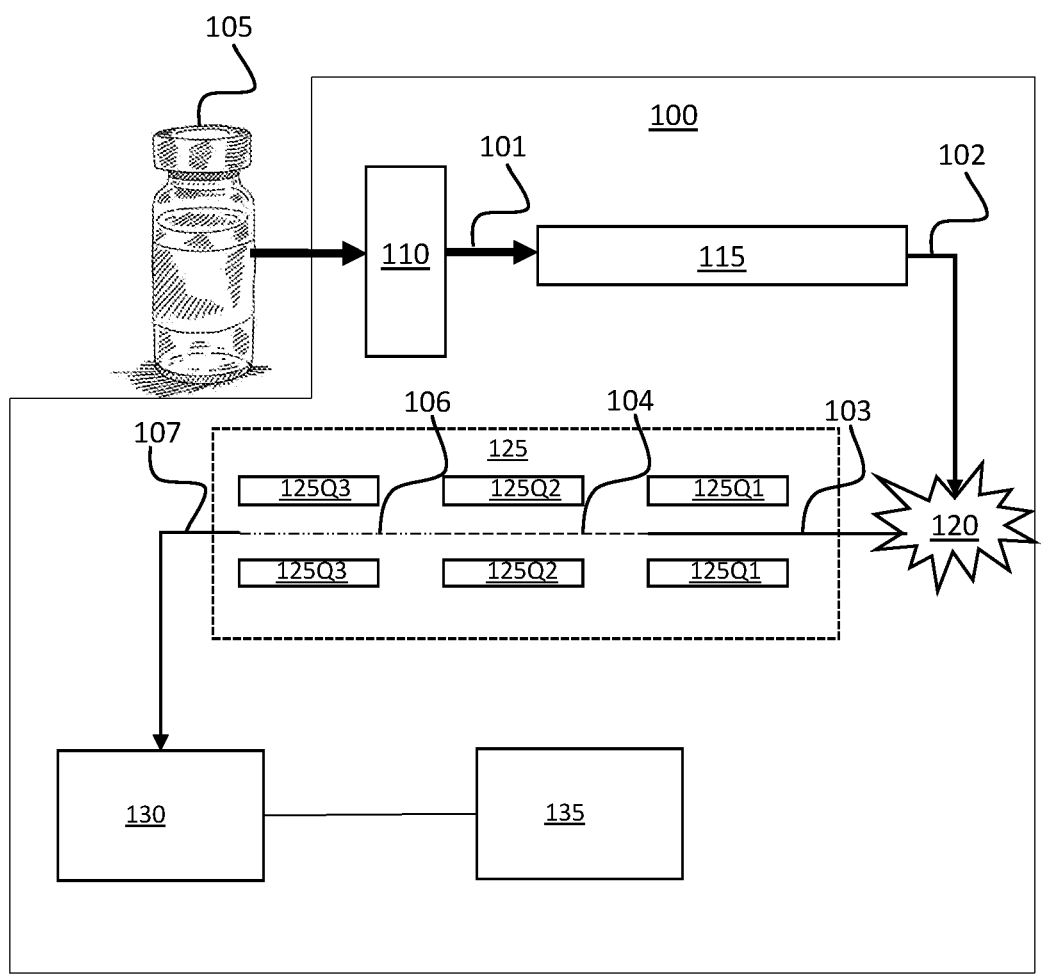
FIG. 1 depicts a block diagram of components of an LC/MS/MS system used to determine concentrations and amounts of PFAS analytes in solutions and/or unconcentrated samples, in accordance with an exemplary embodiment of the present invention.

Currently, the quantitative determination of low levels of the PFAS analytes in water sources often requires extraction of the PFAS analytes from the water. This requirement is typically due to the limitations of the analytical methods employed for sample analysis. When analyte concentrations are too low to be quantitated by established analytical techniques, extraction thereof serves to provide a more concentrated sample than the originally collected unconcentrated water sample. These extraction steps are often time-consuming, costly, and inherently introduce the possibility of errors in the analysis along with an increase in possible sample contamination. In some cases, up to one liter of water from a contaminated water source must be extracted to provide 1 mL of an aqueous sample after evaporation of extracting solvent and subsequent aqueous dissolution of the isolated extract.

Embodiments of the present invention recognize that extraction steps contribute to increased costs and errors in the qualitative and quantitative analysis of PFAS analytes in water samples. Embodiments of the present invention provide a method and LC/MS/MS system for the determination of concentrations and amounts of low levels of PFAS analytes in unconcentrated as well as concentrated samples. Thus, extraction techniques may be avoided in the analysis of PFAS analytes in unconcentrated samples, such as finished drinking water, ground water, raw source water, and water at an intermediate stage of treatment between raw source water and finished drinking water.

As described herein, "PFAS analyte" indicates a poly- or perfluorinated alkyl carboxylic or sulfonic acid and/or the corresponding conjugate bases. It will be readily understood by one having ordinary skill in the art that the relative quantity of the acid and conjugate base will be dependent on the pH of the sample and/or standard that contains the PFAS analyte as well as the pKa(H2O) of the PFAS acid component within the given sample and/or standard solution.

The PFAS analytes, as acids and/or the corresponding conjugate bases, that are detected in a solution or an unconcentrated sample include without limitation: i) perfluorobutanoic acid (C3F7CO2H) and/or the conjugate base thereof, i.e., perfluorobutanoate (C3F7CO2-); ii) perfluorobutanesulfonic acid (C4F9SO3H) and/or the conjugate base thereof, i.e., perfluorobutane sulfonate (C4F9SO3-); iii) perfluoropentanesulfonic acid (C5F11SO3H) and/or the conjugate base thereof, i.e., perfluoropentane sulfonate (C5F11SO3-); iv) perfluorohexanoic acid (C5F11CO2H) and/or the conjugate base thereof, i.e., perfluorohexanoate (C5F11CO2-); v) perfluorohexanesulfonic acid (C6F13SO3H) and/or the conjugate base thereof, i.e., perfluorohexane sulfonate (C6F13SO3-); vi) perfluoroheptanoic acid (C6F13CO2H) and/or the conjugate base thereof, i.e., perfluoroheptanoate (C6F13CO2-); vii) perfluoroheptanesulfonic acid (C7F15SO3H) and/or the conjugate base thereof, i.e., perfluoroheptane sulfonate (C7F15SO3-); viii) perfluorooctanoic acid (C7F15CO2H) and/or the conjugate base thereof, i.e., perfluorooctanoate (C7F15CO2-); ix) perfluorooctanesulfonic acid (C8F17SO3H) and/or the conjugate base thereof, i.e., perfluorooctane sulfonate (C8F17SO3-); x) perfluorononanoic acid (C8F17CO2H) and/or the conjugate base thereof, i.e., perfluorononanoate (C8F17CO2-); and xi) perfluorodecanoic acid (C9F19CO2H) and/or the conjugate base thereof, i.e., perfluorodecanoate (C9F19CO2-).

The method and system encompasses the concentration determination of, in a solution or an unconcentrated sample, all known isomers of PNAS analytes with the general formula $C_nF_{(2n+1)}$—X as described herein.

PFAS analyte acronyms used throughout this description are as shown in Table 1.

TABLE 1

| Acronym Definitions. | |
|---|---|
| Analyte Name (Acid/Conjugate Base) | Acronym |
| Perfluorobutanoic acid/Perfluorobutanoate | PFBA |
| Perfluorobutanesulfonic acid/Perfluorobutane sulfonate | PFBS |

TABLE 1-continued

Acronym Definitions.

| Analyte Name (Acid/Conjugate Base) | Acronym |
|---|---|
| Perfluorodecanoic acid/Perfluorodecanoate | PFDA |
| Perfluoroheptanoic acid/Perfluoroheptanoate | PFHpA |
| Perfluoroheptanesulfonic acid/Perflorohe ptanesulfonate | PFHpS |
| Perfluorohexanoic acid/Perfluorohexanoate | PFHxA |
| Perfluorohexanesulfonic acid/Perflorohexanesulfonate | PFHxS |
| Perfluorononanoic acid/Perfluorononanoate | PFNA |
| Perfluoropentanesulfonic acid/Perfloropentanesulfonate | PFPeS |
| Perfluorooctanoic acid/Perfluorooctanoate | PFOA |
| Perfluorooctanesulfonic acid/Perflorooctanesulfonate | PFOS |

Certain exemplary embodiments will now be described to provide an overall understanding of the principles of the structure, function, and use of the methods and systems disclosed herein. One or more examples of these embodiments are illustrated in the accompanying drawings. Those skilled in the art will understand that the methods and systems specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "substantially", "approximately", "about", "relatively," or other such similar terms that may be used throughout this disclosure, including the claims, are used to describe and account for small fluctuations, such as due to variations in processing. For example, they can refer to less than or equal to +10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The ranges disclosed herein include increments governed by significant figures as recited in the ranges. For example, a temperature range of approximately 120° C. to approximately 125° C. indicates three significant figures, hence approximately 120 to approximately 121° C., approximately 121 to approximately 122° C., approximately 122 to approximately 123° C., approximately 123 to approximately 124° C., and approximately 124 to approximately 125° C. are thereby included as range subsets.

In various embodiments, unconcentrated samples are analyzed for detection and quantitation of PFAS analytes. As used herein, "unconcentrated sample" typically refers to an aqueous sample collected from a water source such as, but not limited to, finished drinking water, ground water, raw source water, and water at an intermediate stage of treatment between raw source water and finished drinking water. The sample may also be collected from an effluent from processes that utilize one or more PFAS analytes, such as from a factory that produces PFAS-containing products. The unconcentrated sample is not concentrated by any deliberate or substantial evaporation of the solvent, i.e., water. Further, the unconcentrated sample is not concentrated by, for example, extraction into an organic solvent to subsequently make a non-aqueous or aqueous solution of PFAS analyte(s) that have higher concentrations than the originally collected sample. An unconcentrated sample also includes a sample that is diluted with respect to the originally collected sample. The diluent may be water or a water-miscible solvent such as, but not limited to, an alcohol (e.g., methanol, ethanol, n-propanol, isopropanol, n-butanol sec-butanol, iso-butyl alcohol, tert-butyl alcohol, diols such as ethylene glycol, triols such as glycerol, etc.), acetonitrile, etc. In some embodiments, unconcentrated samples also contain added chemicals, such as ammonium chloride, buffers, etc., for purposes of dechlorination, sample preservation, pH adjustment, etc.

Unconcentrated samples include such water samples which are not diluted or concentrated such that they may be directly injected from the source, with or without minimal processing, into the system for analysis. The term "minimal processing" includes the addition of preservatives, buffers, etc. in order to modulate sample stability, pH, etc.

In various embodiments, concentrated samples are analyzed for detection and quantitation of PFAS analyte(s) at extremely low levels. As used herein, "concentrated samples" include samples obtained via one or more of the following steps: i) the extraction of PFAS analyte(s) from a first volume of water (typically an aqueous sample obtained directly from a water source) into second volume of a water-immiscible solvent, wherein the second volume of a water-immiscible solvent is less than or substantially the same; ii) partial or complete evaporation of the water-immiscible solvent to concentrate the PFAS analyte(s) contained therein; and iii) re-dissolving the PFAS analyte(s) into a third volume of water with or without the concomitant introduction of preservatives, buffers, and/or dechlorination agents, wherein the third volume of water is of a lesser volume than the first volume of water.

In some embodiments of the present invention, concentrated and unconcentrated samples of PFAS analyte(s) include samples collected and prepared from soil and plants, as described elsewhere (e.g., see Huset and Barry, "Quantitative determination of perfluoroalkyl substances (PFAS) in soil, water, and home garden produce", MethodsX 5 (2018) 697-704). In some embodiments, concentrated and unconcentrated samples of PFAS analyte(s) include samples collected from urine and blood.

As used herein, the term "PFAS analyte solution," "PFAS analyte(s) in a solution," "a solution containing PFAS analyte(s)," and the like, includes a homogeneous solution of PFAS analyte(s), which includes concentrated and unconcentrated PFAS analyte samples as well as standards, etc. As is well-known in the art, for any analyte to be injected onto an LC/MS/MS system, it must be in a homogeneous solution of a solvent suitable for injection onto an LC column.

It will be understood that within a known volume of an analyte solution that has a known concentration, the amount of analyte is also known and readily calculated. For example, 75 microliters ($\propto L$ or $\propto l$) of a PFAS analyte solution that has a concentration of 0.010 micrograms per liter (0.010 $\propto$g/L or $\propto$g/l) contains $7.5 \times 10^{-7}$ $\propto$g of the PFAS analyte according to the equation: $(0.010\ \propto g/L) \times (75\ \propto L) \times (10\text{-}6\ L/\propto L) = 7.5 \times 10^{-7}\ \propto g$. Thus, 75 $\propto$L of a 0.0020 $\propto$g/L PFAS analyte solution contains $1.5 \times 10^{-7}$ $\propto$g of the PFAS analyte, 75 $\propto$L of a 0.25 $\propto$g/L PFAS analyte solution contains $1.9 \times 10^{-5}$ $\propto$g of the PFAS analyte and 75 $\propto$L of a 0.070 $\propto$g/L PFAS analyte solution contains $5.3 \times 10^{-6}$ $\propto$g of the PFAS analyte.

Throughout this description and claims, it will be understood that any known volume of an analyte solution with a known concentration of said analyte may be expressed in terms of a known mass of said analyte.

Herein, analyte concentration may be expressed as parts per trillion (ppt) according to the relationship 1 ng/L=1 ppt. Thus, 0.010 µg/L may be expressed as 10 ppt, 0.0020 µg/L may be expressed as 2 ppt, 0.070 µg/L may be expressed as 70 ppt, and 0.25 µg/L may be expressed as 250 ppt. Because the relationship between ppt and µg/L is defined above, it is now established that a known volume containing a known ppt of an analyte may also be expressed in terms of a known mass of said analyte.

Embodiments of the present invention provide a method and system to determine the concentration of a PFAS analyte of formula CnF(2n+1)—X in solutions such as unconcentrated samples within a range of approximately 0.0020 µg/L to approximately 0.25 µg/L based on approximately a 75 µL injection volume using ESI conditions on an LC/MS/MS instrument as described infra. It will be readily apparent to one skilled in the art that, since the sensitivity of the method and system described herein is dependent on injection volume, injection volumes greater than approximately 75 µL will produce quantitation of solutions having a concentration of PFAS analyte of formula CnF(2n+1)—X in solutions that is lower than 0.0020 ∝g/L. In some embodiments, a concentration of a PFAS analyte of formula $C_nF_{(2n+1)}$—X in solutions such as unconcentrated samples is determined within a range of approximately 0.0020 ∝g/L to approximately 0.24 ∝g/L. In some embodiments, the range is approximately 0.0020 ∝g/L to approximately 0.23 ∝g/L. In some embodiments, the range is approximately 0.0020 ∝g/L to approximately 0.22 ∝g/L. In some embodiments, the range is approximately 0.0020 ∝g/L to approximately 0.21 ∝g/L. In some embodiments, the range is approximately 0.0020 ∝g/L to approximately 0.20 ∝g/L. In some embodiments, the range is approximately 0.0020 ∝g/L to approximately 0.19 ∝g/L. In some embodiments, the range is approximately 0.0020 ∝g/L to approximately 0.18 ∝g/L. In some embodiments, the range is approximately 0.0020 ∝g/L to approximately 0.17 ∝g/L. In some embodiments, the range is approximately 0.0020 ∝g/L to approximately 0.16 ∝g/L. In some embodiments, the range is approximately 0.0020 ∝g/L to approximately 0.15 ∝g/L. In some embodiments, the range is approximately 0.0020 ∝g/L to approximately 0.14 cc g/L. In some embodiments, the range is approximately 0.0020 ∝g/L to approximately 0.13 ∝g/L. In some embodiments, the range is approximately 0.0020 ∝g/L to approximately 0.12 ∝g/L. In some embodiments, the range is approximately 0.0020 ∝g/L to approximately 0.11 ∝g/L. In some embodiments, the range is approximately 0.0020 ∝g/L to approximately 0.10 ∝g/L. In some embodiments, the range is approximately 0.0020 ∝g/L to approximately 0.090 ∝g/L. In some embodiments, the range is approximately 0.0020 ∝g/L to approximately 0.080 ∝g/L. In some embodiments, the range is approximately 0.0020 ∝g/L to approximately 0.070 ∝g/L. In some embodiments, the range is approximately 0.0020 ∝g/L to approximately 0.060 ∝g/L. In some embodiments, the range is approximately 0.0020 ∝g/L to approximately 0.050 ∝g/L. In some embodiments, the range is approximately 0.0020 ∝g/L to approximately 0.040 ∝g/L. In some embodiments, the range is approximately 0.0020 ∝g/L to approximately 0.030 ∝g/L. In some embodiments, the range is approximately 0.0020 ∝g/L to approximately 0.020 ∝g/L. In some embodiments, the range is approximately 0.0020 ∝g/L to approximately 0.010 ∝g/L.

Embodiments of the present invention provide a method and system to determine a concentration of a PFAS analyte of formula CnF(2n+1)—X in solutions such as unconcentrated samples within a range of approximately 0.010 µg/L to approximately 0.25 µg/L based on a 75 µL injection volume using ESI conditions on an LC/MS/MS instrument as described infra.

In some embodiments, a concentration of a PFAS analyte of formula CnF(2n+1)—X in solutions such as unconcentrated samples is determined within a range of approximately 0.010 µg/L to approximately 0.24 µg/L. In some embodiments, the range is approximately 0.010 µg/L to approximately 0.23 µg/L. In some embodiments, the range is approximately 0.010 µg/L to approximately 0.22 µg/L. In some embodiments, the range is approximately 0.010 µg/L to approximately 0.21 µg/L. In some embodiments, the range is approximately 0.010 µg/L to approximately 0.20 µg/L. In some embodiments, the range is approximately 0.010 µg/L to approximately 0.19 µg/L. In some embodiments, the range is approximately 0.010 µg/L to approximately 0.18 µg/L. In some embodiments, the range is approximately 0.010 µg/L to approximately 0.17 µg/L. In some embodiments, the range is approximately 0.010 µg/L to approximately 0.16 µg/L. In some embodiments, the range is approximately 0.010 µg/L to approximately 0.15 µg/L. In some embodiments, the range is approximately 0.010 µg/L to approximately 0.14 µg/L. In some embodiments, the range is approximately 0.010 µg/L to approximately 0.13 µg/L. In some embodiments, the range is approximately 0.010 µg/L to approximately 0.12 µg/L. In some embodiments, the range is approximately 0.010 µg/L to approximately 0.11 µg/L. In some embodiments, the range is approximately 0.010 µg/L to approximately 0.10 µg/L. In some embodiments, the range is approximately 0.010 µg/L to approximately 0.090 µg/L. In some embodiments, the range is approximately 0.010 µg/L to approximately 0.080 µg/L. In some embodiments, the range is approximately 0.010 µg/L to approximately 0.070 µg/L. In some embodiments, the range is approximately 0.010 µg/L to approximately 0.060 µg/L. In some embodiments, the range is approximately 0.010 µg/L to approximately 0.050 µg/L. In some embodiments, the range is approximately 0.010 µg/L to approximately 0.040 µg/L. In some embodiments, the range is approximately 0.010 µg/L to approximately 0.030 µg/L. In some embodiments, the range is approximately 0.010 µg/L to approximately 0.020 µg/L.

Embodiments of the present invention provide a method and system to determine a concentration of a PFAS analyte of formula CnF(2n+1)—X in solutions such as unconcentrated samples within a range of approximately 0.070 µg/L to approximately 0.25 µg/L based on a 75 µL injection volume using ESI conditions on an LC/MS/MS instrument as described infra.

In some embodiments, a concentration of a PFAS analyte of formula CnF(2n+1)—X in solutions such as unconcentrated samples is determined within a range of approximately 0.070 µg/L to approximately 0.24 µg/L. In some embodiments, the range is approximately 0.070 µg/L to approximately 0.23 µg/L. In some embodiments, the range is approximately 0.070 µg/L to approximately 0.22 µg/L. In some embodiments, the range is approximately 0.070 µg/L to approximately 0.21 µg/L. In some embodiments, the range is approximately 0.070 µg/L to approximately 0.20 µg/L. In some embodiments, the range is approximately 0.070 µg/L to approximately 0.19 µg/L. In some embodiments, the range is approximately 0.070 µg/L to approximately 0.18 µg/L. In some embodiments, the range is approximately 0.070 µg/L to approximately 0.17 µg/L. In some embodiments, the range is approximately 0.070 µg/L to approximately 0.16 µg/L. In some embodiments, the range is approximately 0.070 µg/L to approximately 0.15 µg/L. In some embodiments, the range is approximately 0.070 µg/L to approximately 0.14 µg/L. In some embodiments, the range is approximately 0.070 µg/L to approximately 0.13 µg/L. In some embodiments, the range is approximately 0.070 µg/L to approximately 0.12 µg/L. In some embodiments, the range is approximately 0.070 µg/L to approximately 0.11 µg/L. In some embodiments, the range is approximately 0.070 µg/L to approximately 0.10 µg/L. In some embodiments, the range is approximately 0.070 µg/L to approximately 0.090 µg/L. In some embodiments, the range is approximately 0.070 µg/to approximately 0.080 µg/L.

Embodiments of the present invention provide a method and system to determine a concentration of a PFAS analyte of formula $CnF(2n+1)$—X in solutions such as unconcentrated samples within a range of approximately 2.0 ppt to approximately 250 ppt based on a 75 µL injection volume using ESI conditions on an LC/MS/MS instrument as described infra. As explained supra, wherein 1 ng/L=1 ppt (i.e. 1.0 µg/L=1.0×103 ppt), the embodiments described supra of determinable µg/L concentration ranges of PFAS analytes apply when expressed as ppt.

It will be readily understood by a person having ordinary skill in the art that virtually any concentration of a PFAS analyte of formula $CnF(2n+1)$—X above 0.250 µg/L (250.0 ppt) within a solution is determinable by the method and system described herein via the use of well-known dilution techniques. In fact, such techniques are exemplified by the preparation of analyte standards as described infra.

Embodiments of the present invention provide a method and system to determine an amount of a PFAS analyte of formula $CnF(2n+1)$—X that is injected from a solution such as unconcentrated sample onto an LC/MS/MS instrument based on a known injected volume of determined concentration. The individual amount of a PFAS analyte that are determinable per injection range from approximately $1.5 \times 10^{-7}$ µg to approximately $1.9 \times 10^{-5}$ µg using ESI conditions as described infra.

In some embodiments, the amount of a PFAS analyte determinable per injection is within a range of approximately $1.5 \times 10^{-7}$ µg to approximately $1.8 \times 10^{-5}$ µg. In some embodiments, the determinable amount is within a range of approximately $1.5 \times 10^{-7}$ µg to approximately $1.7 \times 10^{-5}$ µg. In some embodiments, the determinable amount is within a range of approximately $1.5 \times 10^{-7}$ µg to approximately $1.6 \times 10^{-5}$ µg. In some embodiments, the determinable amount is within a range of approximately $1.5 \times 10^{-7}$ µg to approximately $1.5 \times 10^{-5}$ µg. In some embodiments, the determinable amount is within a range of approximately $1.5 \times 10^{-7}$ µs to approximately $1.4 \times 10^{-5}$ µg. In some embodiments, the determinable amount is within a range of approximately $1.5 \times$ µg to approximately $1.3 \times 10^{-5}$ µg. In some embodiments, the determinable amount is within a range of approximately $1.5 \times 10^{-7}$ fig to approximately $1.2 \times 10^{-5}$ µg. In some embodiments, the determinable amount is within a range of approximately $1.5 \times 10^{-7}$ µs to approximately $1.1 \times 10^{-5}$ µg. In some embodiments, the determinable amount is within a range of approximately $1.5 \times 10^{-7}$ µg to approximately $9.8 \times 10^{-6}$ µg. In some embodiments, the determinable amount is within a range of approximately $1.5 \times 10^{-7}$ µg to approximately $9.0 \times 10^{-6}$ µg. In some embodiments, the determinable amount is within a range of approximately $1.5 \times 10^{-7}$ µs to approximately $8.3 \times 10^{-6}$ µg. In some embodiments, the determinable amount is within a range of approximately $1.5 \times 10^{-7}$ µg to approximately $7.5 \times 10^{-6}$ µg. In some embodiments, the determinable amount is within a range of approximately $1.5 \times 10^{-7}$ fig to approximately $6.8 \times 10^{-6}$ µg. In some embodiments, the determinable amount is within a range of approximately $1.5 \times 10^{-7}$ µg to approximately $6.0 \times 10^{-6}$ µg. In some embodiments, the determinable amount is within a range of approximately $1.5 \times 10^{-7}$ µg to approximately $5.3 \times 10^{-6}$ µg. In some embodiments, the determinable amount is within a range of approximately $1.5 \times 10^{-7}$ µg to approximately $4.5 \times 10^{-6}$ µg. In some embodiments, the determinable amount is within a range of approximately $1.5 \times 10^{-7}$ µg to approximately $3.8 \times 10^{-6}$ µg. In some embodiments, the determinable amount is within a range of approximately $1.5 \times 10^{-7}$ µg to approximately $3.0 \times 10^{-6}$ µg. In some embodiments, the determinable amount is within a range of approximately $1.5 \times 10^{-7}$ µg to approximately $2.3 \times 10^{-6}$ µg. In some embodiments, the determinable amount is within a range of approximately $1.5 \times 10^{-7}$ µg to approximately $1.5 \times 10^{-6}$ µg. In some embodiments, the determinable amount is within a range of approximately $1.5 \times 10^{-7}$ µg to approximately $7.5 \times 10^{-7}$ µg.

Embodiments of the present invention provide a method and system to determine an amount of a PFAS analyte of formula $CnF(2n+1)$—X that is injected from a solution such as unconcentrated sample onto an LC/MS/MS instrument based on a known injected volume of determined concentration. The individual amount of a PFAS analyte that are determinable per injection range from approximately $7.5 \times 10^{-7}$ µg to approximately $1.9 \times 10^{-5}$ µg using ESI conditions as described infra.

In some embodiments, the amount of a PFAS analyte determinable per injection is within a range of approximately $7.5 \times 10^{-7}$ µg to approximately $1.8 \times 10^{-5}$ µg. In some embodiments, the determinable amount is within a range of approximately $7.5 \times 10^{-7}$)µg to approximately $1.7 \times 10^{-5}$ µg. In some embodiments, the determinable amount is within a range of approximately $7.5 \times 10^{-7}$ µg to approximately $1.6 \times 10^{-5}$ µg. In some embodiments, the determinable amount is within a range of approximately $7.5 \times 10^{-7}$ µg to approximately $1.5 \times 10^{-5}$ µg. In some embodiments, the determinable amount is within a range of approximately $7.5 \times 10^{-7}$ µg to approximately $1.4 \times 10^{-5}$ µg. In some embodiments, the determinable amount is within a range of approximately $7.5 \times 10^{-7}$ µg to approximately $1.3 \times 10^{-5}$ µg. In some embodiments, the determinable amount is within a range of approximately $7.5 \times 10^{-7}$ µg to approximately $1.2 \times 10^{-5}$ µg. In some embodiments, the determinable amount is within a range of approximately $7.5 \times 10^{-7}$ µg to approximately $1.1 \times 10^{-5}$ µg. In some embodiments, the determinable amount is within a range of approximately $7.5 \times 10^{-7}$ µg to approximately $9.8 \times 10^{-6}$ µg. In some embodiments, the determinable amount is within a range of approximately $7.5 \times 10^{-7}$ µg to approximately $9.0 \times 10^{-6}$ µg. In some embodiments, the determinable amount is within a range of approximately $7.5 \times 10^{-7}$ µg to approximately $8.3 \times 10^{-6}$ µg. In some embodiments, the determinable amount is within a range of approximately $7.5 \times 10^{-7}$ µg to approximately $7.5 \times 10^{-6}$ µg. In some embodiments, the determinable amount is within a range of approximately $7.5 \times 10^{-7}$ µg to approximately $6.8 \times 10^{-6}$ µg. In some embodiments, the determinable amount is within a range of approximately $7.5 \times 10^{-7}$ µg to approximately $6.0 \times 10^{-6}$ µg. In some embodiments, the determinable amount is within a range of approximately $7.5 \times 10^{-7}$ µg to approximately $5.3 \times 10^{-6}$ µg. In some embodiments, the determinable amount is within a range of approximately $7.5 \times 10^{-7}$ µg to approximately $4.5 \times 10^{-6}$ µg. In some embodiments, the determinable amount is within a range of approximately $7.5 \times 10^{-7}$ µg to approximately $3.8 \times 10^{-6}$ µg. In some embodiments, the determinable amount is within a range of approximately $7.5 \times 10^{-7}$ µg to approximately $3.0 \times 10^{-6}$ µg. In some embodiments, the determinable amount is within a range of approximately $7.5 \times 10^{-7}$ µg to approximately $2.3 \times 10^{-6}$ µg. In some embodiments, the determinable amount is within a range of approximately $7.5 \times 10^{-7}$ µg to approximately $1.5 \times 10^{-6}$ µg.

Embodiments of the present invention provide a method and system to determine an amount of a PFAS analyte of formula $CnF(2n+1)$—X that is injected from a solution such as unconcentrated sample onto an LC/MS/MS instrument based on a known injected volume of determined concentration. The individual amount of a PFAS analyte that are determinable per injection range from approximately $5.3 \times 10^{-6}$ µg to approximately $1.9 \times 10^{-5}$ µg using ESI conditions as described infra.

In some embodiments, the amount of a PFAS analyte determinable per injection is within a range of approximately $5.3 \times 10^{-6}$ µg to approximately $1.8 \times 10^{-5}$ µg. In some embodiments, the determinable amount is within a range of approximately $5.3 \times 10^{-6}$ µg to approximately $1.7 \times 10^{-5}$ µg. In some embodiments, the determinable amount is within a range of approximately $5.3 \times 10^{-6}$ µg to approximately $1.6 \times 10^{-5}$ µg. In some embodiments, the determinable amount is within a range of approximately $5.3 \times 10^{-6}$ µg to approximately $1.5 \times 10^{-5}$ µg. In some embodiments, the determinable amount is within a range of approximately $5.3 \times 10^{-6}$ µg to approximately $1.4 \times 10^{-5}$ µg. In some embodiments, the determinable amount is within a range of approximately $5.3 \times 10^{-6}$ µg to approximately $1.3 \times 10^{-5}$ µg. In some embodiments, the determinable amount is within a range of approximately $5.3 \times 10^{-6}$ µg to approximately $1.2 \times 10^{-5}$ µg. In some embodiments, the determinable amount is within a range of approximately $5.3 \times 10^{-6}$ fig to approximately $1.1 \times 10^{-5}$ µg. In some embodiments, the determinable amount is within a range of approximately $5.3 \times 10^{-6}$ µg to approximately $9.8 \times 10^{-6}$ µg. In some embodiments, the determinable amount is within a range of approximately $5.3 \times 10^{-6}$ lag to approximately $9.0 \times 10^{-6}$ FIG. 1n some embodiments, the determinable amount is within a range of approximately $5.3 \times 10^{-6}$ µg to approximately $8.3 \times 10^{-6}$ µg. In some embodiments, the determinable amount is within a range of approximately $5.3 \times 10^{-6}$ µg to approximately $7.5 \times 10^{-6}$ µg. In some embodiments, the determinable amount is within a range of approximately $5.3 \times 10^{-6}$ µg to approximately $6.8 \times 10^{-6}$ FIG. 1n some embodiments, the determinable amount is within a range of approximately $5.3 \times 10^{-6}$ µg to approximately $6.0 \times 10^{-6}$ µg.

Embodiments of the present invention utilize ESI on an LC/MS/MS system to determine PFAS analyte concentration and amount. ESI is an ionization technique used in mass spectrometry to produce ions using an electrospray in which a high voltage is applied to a liquid to create an aerosol that is ionized.

FIG. 1 depicts a block diagram of components 100 of an LC/MS/MS system used to determine a concentration and/or amount of a PFAS analyte in samples in accordance with an exemplary embodiment of the present invention. It should be appreciated that FIG. 1 provides only an illustration of one implementation and does not imply any limitations with regard to other systems in which embodiments of the present invention may be implemented. Other modifications to the depicted system may be made without departing from the scope of the present invention.

LC/MS/MS system 100 includes injector 110, LC column 115, ESI ionizer component 120, triple quadrupole mass spectrometer (TQMS) component 125, ion detector 130, and mass spectrum read-out software 135.

TQMS 125 includes two quadrupole mass analyzers in series (125Q1 and 125Q3) with a non-mass-resolving quadrupole (125Q2) between them to act as a cell for collision-induced dissociation. All three quadrupole mass analyzers consist of four cylindrical rods (for reasons of simplicity they are schematically represented by the labeled parallel bars in FIG. 1). The four cylindrical bars are set parallel to each other. For 125Q1 and 125Q3, each opposing rod pair is connected together electrically and a radio frequency (RF) voltage with a DC offset voltage is applied between one pair of rods and the other. Ions travel down the quadrupole between the rods. Only ions of a certain mass-to-charge ratio will reach detector 130 for a given ratio of voltages. Other ions have unstable trajectories and will collide with the rods. This permits selection of an ion with a particular m/z or allows the operator to scan for a range of m/z-values by continuously varying the applied voltage. Quadrapole 125Q2 is an RF-only quadrupole (non-mass filtering) for collision induced dissociation of selected parent ion(s) from 125Q1. Subsequent fragments are passed through to 125Q3 where they may be filtered or fully scanned.

In an embodiment, an aliquot of PFAS analyte sample 105 is injected into injector 110 and the injection liquid 101 is resolved into various PFAS analytes by LC column 115 using, for example, the column, conditions, and gradient example shown and described for Table 6.

After eluting through LC column 115, the PFAS analyte-containing eluent 102 is subjected to ESI 120. Conditions for ionization of PFAS analytes using ESI techniques as depicted by ESI 120 will be detailed and described infra in embodiments of the present invention.

After ionization of the PFAS-containing eluent by ESI 120, the ion(s) 103 are passed through the first quadrupole mass analyzer, 125Q1, which serves as a filter for selecting desired PFAS analyte ions 104. The second quadrupole mass analyzer, 125Q2, allows for collision of selected ions 104 to produce one or more children ions 106 that then pass through the third quadrupole mass analyzer, 125Q3. Quadrupole mass analyzer 125Q3 provides a scan of the entire m/z range of the product ion(s) 106, providing output 107 for fragments 106. Quantification of selected ion 104 can then be deduced from the ion fragmentation output 107 received by ion detector 130 and processed by mass spectrum read-out software 135.

Embodiments of the present invention employ ESI settings on an LC/MS/MS system such as the system described above that include: i) an ion polarity setting to cause the formation of negative or positive ions; ii) a probe gas temperature setting for controlling the temperature of an inert drying gas (typically nitrogen) that is used to promote the removal of solvent from aerosol particles in spray ionization; iii) a gas flow setting for controlling the volume per unit time that the drying gas is dispersed; iv) a nebulizer setting for controlling the pressure utilized for the mass spectrometer nebulizer, which delivers a fine mist using the specified pressure; v) a sheath gas heater setting for controlling a temperature setting for heating a sheath gas, which is an inert gas (typically nitrogen) introduced through a tube that is coaxial with the electrospray emitter to pneumatically assist the formation of the sprayed droplets; vi) a sheath gas flow setting for controlling a volume per unit time that the sheath gas is dispersed; vii) a capillary voltage setting for controlling a voltage applied to the tip of a metal capillary relative to the surrounding source-sampling cone or heated capillary, which creates a strong electric field causes the dispersion of the sample solution into an aerosol of highly charged electrospray droplets; and viii) a V charging setting for controlling a charging electrode within the instrument.

A non-limiting example of ESI settings used on an AGILENT 6495 mass spectrometer for analyzing concentrations and amounts of PFAS analytes in solutions such as unconcentrated samples is shown in Table 2 below.

TABLE 2

Example of ESI settings used in an embodiment of the present invention.

| Polarity | Negative ion |
|---|---|
| ESI Conditions | |
| Gas Temp (° C.) | 120 |
| Gas Flow (1/min) | 11 |
| Nebulizer (psi) | 20 |
| Sheath Gas Heater | 400 |
| Sheath Gas Flow | 8 |
| Capillary (V) | 1500 |
| V Charging | 0 |
| Ion Funnel Parameters | |
| High Pressure RF | 110 |
| Low Pressure RF | 80 |

For Table 2 above, the "Ion Funnel Parameters" refers to settings for an ion funnel, which is used to focus a beam of ions using a series of stacked ring electrodes with decreasing inner diameter. A combined radio frequency (RF) and fixed electrical potential is applied to the grids.

In various embodiments of the present invention, concentrations and amounts of PFAS analytes in solutions such as unconcentrated samples are analyzed using ESI conditions include a probe gas temperature setting ("Gas Temp (° C.)") of approximately 120° C. to approximately 180° C. In some embodiments, the probe gas temperature setting is approximately 120° C. to approximately 175° C. In some embodiments, the probe gas temperature setting is approximately 120° C. to approximately 170° C. In some embodiments, the probe gas temperature setting is approximately 120° C. to approximately 165° C. In some embodiments, the probe gas temperature setting is approximately 120° C. to approximately 160° C. In some embodiments, the probe gas temperature setting is approximately 120° C. to approximately 155° C. In some embodiments, the probe gas temperature setting is approximately 120° C. to approximately 150° C. In some embodiments, the probe gas temperature setting is approximately 120° C. to approximately 145° C. In some embodiments, the probe gas temperature setting is approximately 120° C. to approximately 140° C. In some embodiments, the probe gas temperature setting is approximately 120° C. to approximately 135° C. In some embodiments, the probe gas temperature setting is approximately 120° C. to approximately 130° C. In some embodiments, the probe gas temperature setting is approximately 120° C. to approximately 125° C. In some embodiments, the probe gas temperature setting is approximately 120° C.

In some embodiments, ESI conditions include a probe gas temperature setting of approximately 125° C. to approximately 180° C. In some embodiments, the probe gas temperature setting is approximately 125° C. to approximately 175° C. In some embodiments, the probe gas temperature setting is approximately 125° C. to approximately 170° C. In some embodiments, the probe gas temperature setting is approximately 125° C. to approximately 165° C. In some embodiments, ESI conditions include a probe probe gas temperature setting of approximately 125° C. to approximately 160° C. In some embodiments, the probe gas temperature setting is approximately 125° C. to approximately 155° C. In some embodiments, the probe gas temperature setting is approximately 125° C. to approximately 150° C. In some embodiments, the probe gas temperature setting is approximately 125° C. to approximately 145° C. In some embodiments, the probe gas temperature setting is approximately 125° C. to approximately 140° C. In some embodiments, the probe gas temperature setting is approximately 125° C. to approximately 135° C. In some embodiments, the probe gas temperature setting is approximately 125° C. to approximately 130° C. In some embodiments, the probe gas temperature setting is approximately 125° C.

In some embodiments, ESI conditions include a probe gas temperature setting of approximately 130° C. to approximately 180° C. In some embodiments, the probe gas temperature setting is approximately 130° C. to approximately 175° C. In some embodiments, the probe gas temperature setting is approximately 130° C. to approximately 170° C. In some embodiments, the probe gas temperature setting is approximately 130° C. to approximately 165° C. In some embodiments, the probe gas temperature setting is approximately 130° C. to approximately 160° C. In some embodiments, the probe gas temperature setting is approximately 130° C. to approximately 155° C. In some embodiments, the probe gas temperature setting is approximately 130° C. to approximately 150° C. In some embodiments, the probe gas temperature setting is approximately 130° C. to approximately 145° C. In some embodiments, the probe gas temperature setting is approximately 130° C. to approximately 140° C. In some embodiments, the probe gas temperature setting is approximately 130° C. to approximately 135° C. In some embodiments, the probe gas temperature setting is approximately 130° C.

In some embodiments, ESI conditions include a probe gas temperature setting of approximately 135° C. to approximately 180° C. In some embodiments, the probe gas temperature setting is approximately 135° C. to approximately 175° C. In some embodiments, the probe gas temperature setting is approximately 135° C. to approximately 170° C. In some embodiments, the probe gas temperature setting is approximately 135° C. to approximately 165° C. In some embodiments, the probe gas temperature setting is approximately 135° C. to approximately 160° C. In some embodiments, the probe gas temperature setting is approximately 135° C. to approximately 155° C. In some embodiments, the probe gas temperature setting is approximately 135° C. to approximately 150° C. In some embodiments, the probe gas temperature setting is approximately 135° C. to approximately 145° C. In some embodiments, the probe gas temperature setting is approximately 135° C. to approximately 140° C. In some embodiments, the probe gas temperature setting is approximately 135° C.

In some embodiments, ESI conditions include a probe gas temperature setting of approximately 140° C. to approximately 180° C. In some embodiments, the probe gas temperature setting is approximately 140° C. to approximately 175° C. In some embodiments, the probe gas temperature setting is approximately 140° C. to approximately 170° C. In some embodiments, the probe gas temperature setting is approximately 140° C. to approximately 165° C. In some embodiments, the probe gas temperature setting is approximately 140° C. to approximately 160° C. In some embodiments, the probe gas temperature setting is approximately 140° C. to approximately 155° C. In some embodiments, the probe gas temperature setting is approximately 140° C. to approximately 150° C. In some embodiments, the probe gas temperature setting is approximately 140° C. to approximately 145° C. In some embodiments, the probe gas temperature setting is approximately 140° C.

In some embodiments, the probe gas temperature setting is approximately 145° C. to approximately 180° C. In some embodiments, the probe gas temperature setting is approximately 145° C. to approximately 175° C. In some embodiments, the probe gas temperature setting is approximately 145° C. to approximately 170° C. In some embodiments, the probe gas temperature setting is approximately 145° C. to approximately 165° C. In some embodiments, the probe gas temperature setting is approximately 145° C. to approximately 160° C. In some embodiments, the probe gas temperature setting is approximately 145° C. to approximately 155° C. In some embodiments, the probe gas temperature setting is approximately 145° C. to approximately 150° C. In some embodiments, the probe gas temperature setting is approximately 145° C.

In some embodiments, ESI conditions include a probe gas temperature setting of approximately 150° C. to approximately 180° C. In some embodiments, the probe gas temperature setting is approximately 150° C. to approximately 175° C. In some embodiments, the probe gas temperature setting is approximately 150° C. to approximately 170° C. In some embodiments, the probe gas temperature setting is approximately 150° C. to approximately 165° C. In some embodiments, the probe gas temperature setting is approximately 150° C. to approximately 160° C. In some embodiments, the probe gas temperature setting is approximately 150° C. to approximately 155° C. In some embodiments, the probe gas temperature setting is approximately 150° C.

In some embodiments, ESI conditions include a probe gas temperature setting of approximately 155° C. to approximately 180° C. In some embodiments, the probe gas temperature setting is approximately 155° C. to approximately 175° C. In some embodiments, the probe gas temperature setting is approximately 155° C. to approximately 170° C. In some embodiments, the probe gas temperature setting is approximately 155° C. to approximately 165° C. In some embodiments, the probe gas temperature setting is approximately 155° C. to approximately 160° C. In some embodiments, the probe gas temperature setting is approximately 155° C.

In some embodiments, ESI conditions include a probe gas temperature setting of approximately 160° C. to approximately 180° C. In some embodiments, the probe gas temperature setting is approximately 160° C. to approximately 175° C. In some embodiments, the probe gas temperature setting is approximately 160° C. to approximately 170° C. In some embodiments, the probe gas temperature setting is approximately 160° C. to approximately 165° C. In some embodiments, the probe gas temperature setting is approximately 160° C.

In some embodiments, ESI conditions include a probe gas temperature setting of approximately 165° C. to approximately 180° C. In some embodiments, the probe gas temperature setting is approximately 165° C. to approximately 175° C. In some embodiments, the probe gas temperature setting is approximately 165° C. to approximately 170° C. In some embodiments, the probe gas temperature setting is approximately 165° C.

In some embodiments, ESI conditions include a probe gas temperature setting of approximately 170° C. to approximately 180° C. In some embodiments, the probe gas temperature setting is approximately 170° C. to approximately 175° C. In some embodiments, the probe gas temperature setting is approximately 170° C.

In some embodiments, ESI conditions include a probe gas temperature setting of approximately 175° C. to approximately 180° C. In some embodiments, the probe gas temperature setting is approximately 175° C.

In some embodiments, ESI conditions include a probe gas temperature setting of approximately 180° C.

In some embodiments when the PFAS analyte solution includes PFBA as analyte, the probe gas temperature setting ranges from approximately 120° C. to approximately 180° C. In some embodiments when the PFAS analyte solution includes PFBA as analyte, the probe gas temperature setting is approximately 120° C.

In some embodiments when the PFAS analyte solution contains PFBS as analyte, the probe gas temperature setting ranges from approximately 120° C. to approximately 180° C. In some embodiments when the PFAS analyte solution includes PFBS as analyte, the probe gas temperature setting is approximately 120° C.

In some embodiments when the PFAS analyte solution contains PFHpA as analyte, the probe gas temperature setting ranges from approximately 120° C. to approximately 180° C. In some embodiments when the PFAS analyte solution includes PFHpA as analyte, the probe gas temperature setting is approximately 120° C.

In some embodiments when the PFAS analyte solution contains PFHxA as analyte, the probe gas temperature setting ranges from approximately 120° C. to approximately 180° C. In some embodiments when the PFAS analyte solution includes PFHxA as analyte, the probe gas temperature setting is approximately 120° C.

In some embodiments when the PFAS analyte solution contains PFHxS as analyte, the probe gas temperature setting ranges from approximately 120° C. to approximately 180° C. In some embodiments when the PFAS analyte solution includes PFHxS as analyte, the probe gas temperature setting is approximately 120° C.

In some embodiments when the PFAS analyte solution contains PFPeS as analyte, the probe gas temperature setting ranges from approximately 120° C. to approximately 180° C. In some embodiments when the PFAS analyte solution includes PFPeS as analyte, the probe gas temperature setting is approximately 120° C.

In some embodiments when the PFAS analyte solution contains PFDA as analyte, the probe gas temperature setting ranges from approximately 120° C. to approximately 160° C. In some embodiments when the PFAS analyte solution includes PFDA as analyte, the probe gas temperature setting is approximately 120° C.

In some embodiments when the PFAS analyte solution contains PFHpS as analyte, the probe gas temperature setting ranges from approximately 120° C. to approximately 160° C. In some embodiments when the PFAS analyte solution includes PFHpS as analyte, the probe gas temperature setting is approximately 120° C.

In some embodiments when the PFAS analyte solution contains PFOS as analyte, the probe gas temperature setting ranges from approximately 120° C. to approximately 160° C. In some embodiments when the PFAS analyte solution includes PFOS as analyte, the probe gas temperature setting is approximately 120° C.

In some embodiments when the PFAS analyte solution contains PFNA as analyte, the probe gas temperature setting ranges from approximately 120° C. to approximately 140° C. In some embodiments when the PFAS analyte solution includes PFNA as analyte, the probe gas temperature setting is approximately 120° C.

In some embodiments when the PFAS analyte solution contains PFNS as analyte, the probe gas temperature setting ranges from approximately 120° C. to approximately 160°

C. In some embodiments when the PFAS analyte solution includes PFNS as analyte, the probe gas temperature setting is approximately 120° C.

In some embodiments when the PFAS analyte solution contains PFOA as analyte, the probe gas temperature setting ranges from approximately 120° C. to approximately 160° C. In some embodiments when the PFAS analyte solution includes PFOA as analyte, the probe gas temperature setting is approximately 120° C.

In some embodiments, the ESI probe gas temperature setting is set on an AGILENT 6490 or 6495 mass spectrometer. In exemplary embodiments, the ESI gas temperature setting is set on an AGILENT 6495 mass spectrometer.

In various embodiments, ESI conditions include a sheath gas heater setting ("Sheath Gas Heater") of approximately 250° C. to approximately 400° C. In some embodiments, the sheath gas heater setting is approximately 250° C. to approximately 395° C. In some embodiments, the sheath gas heater setting is approximately 250° C. to approximately 390° C. In some embodiments, the sheath gas heater setting is approximately 250° C. to approximately 385° C. In some embodiments, the sheath gas heater setting is approximately 250° C. to approximately 380° C. In some embodiments, the sheath gas heater setting is approximately 250° C. to approximately 375° C. In some embodiments, the sheath gas heater setting is approximately 250° C. to approximately 370° C. In some embodiments, the sheath gas heater setting is approximately 250° C. to approximately 365° C. In some embodiments, the sheath gas heater setting is approximately 250° C. to approximately 360° C. In some embodiments, the sheath gas heater setting is approximately 250° C. to approximately 355° C. In some embodiments, the sheath gas heater setting is approximately 250° C. to approximately 350° C. In some embodiments, the sheath gas heater setting is approximately 250° C. to approximately 345° C. In some embodiments, the sheath gas heater setting is approximately 250° C. to approximately 340° C. In some embodiments, the sheath gas heater setting is approximately 250° C. to approximately 335° C. In some embodiments, the sheath gas heater setting is approximately 250° C. to approximately 330° C. In some embodiments, the sheath gas heater setting is approximately 250° C. to approximately 325° C. In some embodiments, the sheath gas heater setting is approximately 250° C. to approximately 320° C. In some embodiments, the sheath gas heater setting is approximately 250° C. to approximately 315° C. In some embodiments, the sheath gas heater setting is approximately 250° C. to approximately 310° C. In some embodiments, the sheath gas heater setting is approximately 250° C. to approximately 305° C. In some embodiments, the sheath gas heater setting is approximately 250° C. to approximately 300° C. In some embodiments, the sheath gas heater setting is approximately 250° C. to approximately 295° C. In some embodiments, the sheath gas heater setting is approximately 250° C. to approximately 290° C. In some embodiments, the sheath gas heater setting is approximately 250° C. to approximately 285° C. In some embodiments, the sheath gas heater setting is approximately 250° C. to approximately 280° C. In some embodiments, the sheath gas heater setting is approximately 250° C. to approximately 275° C. In some embodiments, the sheath gas heater setting is approximately 250° C. to approximately 270° C. In some embodiments, the sheath gas heater setting is approximately 250° C. to approximately 265° C. In some embodiments, the sheath gas heater setting is approximately 250° C. to approximately 260° C. In some embodiments, the sheath gas heater setting is approximately 250° C. to approximately 255° C. In some embodiments, the sheath gas heater setting is approximately 250° C.

In various embodiments, ESI conditions include a sheath gas heater setting of approximately 255° C. to approximately 400° C. In some embodiments, the sheath gas heater setting is approximately 255° C. to approximately 395° C. In some embodiments, the sheath gas heater setting is approximately 255° C. to approximately 390° C. In some embodiments, the sheath gas heater setting is approximately 255° C. to approximately 385° C. In some embodiments, the sheath gas heater setting is approximately 255° C. to approximately 380° C. In some embodiments, the sheath gas heater setting is approximately 255° C. to approximately 375° C. In some embodiments, the sheath gas heater setting is approximately 255° C. to approximately 370° C. In some embodiments, the sheath gas heater setting is approximately 255° C. to approximately 365° C. In some embodiments, the sheath gas heater setting is approximately 255° C. to approximately 360° C. In some embodiments, the sheath gas heater setting is approximately 255° C. to approximately 355° C. In some embodiments, the sheath gas heater setting is approximately 255° C. to approximately 350° C. In some embodiments, the sheath gas heater setting is approximately 255° C. to approximately 345° C. In some embodiments, the sheath gas heater setting is approximately 255° C. to approximately 340° C. In some embodiments, the sheath gas heater setting is approximately 255° C. to approximately 335° C. In some embodiments, the sheath gas heater setting is approximately 255° C. to approximately 330° C. In some embodiments, the sheath gas heater setting is approximately 255° C. to approximately 325° C. In some embodiments, the sheath gas heater setting is approximately 255° C. to approximately 320° C. In some embodiments, the sheath gas heater setting is approximately 255° C. to approximately 315° C. In some embodiments, the sheath gas heater setting is approximately 255° C. to approximately 310° C. In some embodiments, the sheath gas heater setting is approximately 255° C. to approximately 305° C. In some embodiments, the sheath gas heater setting is approximately 255° C. to approximately 300° C. In some embodiments, the sheath gas heater setting is approximately 255° C. to approximately 295° C. In some embodiments, the sheath gas heater setting is approximately 255° C. to approximately 290° C. In some embodiments, the sheath gas heater setting is approximately 255° C. to approximately 285° C. In some embodiments, the sheath gas heater setting is approximately 255° C. to approximately 280° C. In some embodiments, the sheath gas heater setting is approximately 255° C. to approximately 275° C. In some embodiments, the sheath gas heater setting is approximately 255° C. to approximately 270° C. In some embodiments, the sheath gas heater setting is approximately 255° C. to approximately 265° C. In some embodiments, the sheath gas heater setting is approximately 255° C. to approximately 260° C. In some embodiments, the sheath gas heater setting is approximately 255° C.

In various embodiments, ESI conditions include a sheath gas heater setting of approximately 260° C. to approximately 400° C. In some embodiments, the sheath gas heater setting is approximately 260° C. to approximately 395° C. In some embodiments, the sheath gas heater setting is approximately 260° C. to approximately 390° C. In some embodiments, the sheath gas heater setting is approximately 260° C. to approximately 385° C. In some embodiments, the sheath gas heater setting is approximately 260° C. to approximately 380° C. In some embodiments, the sheath gas heater setting is approximately 260° C. to approximately 375° C. In some embodiments, the sheath gas heater setting is approximately 260° C. to approximately 370° C. In some embodiments, the sheath gas heater setting is approximately 260° C. to approximately 365° C. In some embodiments, the sheath gas heater setting is approximately 260° C. to approximately 360° C. In some embodiments, the sheath gas heater setting is approximately 260° C. to approximately 355° C. In some embodiments, the sheath gas heater setting is approximately 260° C. to approximately 350° C. In some embodiments, the sheath gas heater setting is approximately 260° C. to approximately 345° C. In some embodiments, the sheath gas heater setting is approximately 260° C. to approximately 340° C. In some embodiments, the sheath gas heater setting is approximately 260° C. to approximately 335° C. In some embodiments, the sheath gas heater setting is approximately 260° C. to approximately 330° C. In some embodiments, the sheath gas heater setting is approximately 260° C. to approximately 325° C. In some embodiments, the sheath gas heater setting is approximately 260° C. to approximately 320° C. In some embodiments, the sheath gas heater setting is approximately 260° C. to approximately 315° C. In some embodiments, the sheath gas heater setting is approximately 260° C. to approximately 310° C. In some embodiments, the sheath gas heater setting is approximately 260° C. to approximately 305° C. In some embodiments, the sheath gas heater setting is approximately 260° C. to approximately 300° C. In some embodiments, the sheath gas heater setting is approximately 260° C. to approximately 295° C. In some embodiments, the sheath gas heater setting is approximately 260° C. to approximately 290° C. In some embodiments, the sheath gas heater setting is approximately 260° C. to approximately 285° C. In some embodiments, the sheath gas heater setting is approximately 260° C. to approximately 280° C. In some embodiments, the sheath gas heater setting is approximately 260° C. to approximately 275° C. In some embodiments, the sheath gas heater setting is approximately 260° C. to approximately 270° C. In some embodiments, the sheath gas heater setting is approximately 260° C. to approximately 265° C. In some embodiments, the sheath gas heater setting is approximately 260° C.

In various embodiments, ESI conditions include a sheath gas heater setting of approximately 265° C. to approximately 400° C. In some embodiments, the sheath gas heater setting is approximately 265° C. to approximately 395° C. In some embodiments, the sheath gas heater setting is approximately 265° C. to approximately 390° C. In some embodiments, the sheath gas heater setting is approximately 265° C. to approximately 385° C. In some embodiments, the sheath gas heater setting is approximately 265° C. to approximately 380° C. In some embodiments, the sheath gas heater setting is approximately 265° C. to approximately 375° C. In some embodiments, the sheath gas heater setting is approximately 265° C. to approximately 370° C. In some embodiments, the sheath gas heater setting is approximately 265° C. to approximately 365° C. In some embodiments, the sheath gas heater setting is approximately 265° C. to approximately 360° C. In some embodiments, the sheath gas heater setting is approximately 265° C. to approximately 355° C. In some embodiments, the sheath gas heater setting is approximately 265° C. to approximately 350° C. In some embodiments, the sheath gas heater setting is approximately 265° C. to approximately 345° C. In some embodiments, the sheath gas heater setting is approximately 265° C. to approximately 340° C. In some embodiments, the sheath gas heater setting is approximately 265° C. to approximately 335° C. In some embodiments, the sheath gas heater setting is approximately 265° C. to approximately 330° C. In some embodiments, the sheath gas heater setting is approximately 265° C. to approximately 325° C. In some embodiments, the sheath gas heater setting is approximately 265° C. to approximately 320° C. In some embodiments, the sheath gas heater setting is approximately 265° C. to approximately 315° C. In some embodiments, the sheath gas heater setting is approximately 265° C. to approximately 310° C. In some embodiments, the sheath gas heater setting is approximately 265° C. to approximately 305° C. In some embodiments, the sheath gas heater setting is approximately 265° C. to approximately 300° C. In some embodiments, the sheath gas heater setting is approximately 265° C. to approximately 295° C. In some embodiments, the sheath gas heater setting is approximately 265° C. to approximately 290° C. In some embodiments, the sheath gas heater setting is approximately 265° C. to approximately 285° C. In some embodiments, the sheath gas heater setting is approximately 265° C. to approximately 280° C. In some embodiments, the sheath gas heater setting is approximately 265° C. to approximately 275° C. In some embodiments, the sheath gas heater setting is approximately 265° C. to approximately 270° C. In some embodiments, the sheath gas heater setting is approximately 265° C.

In various embodiments, ESI conditions include a sheath gas heater setting of approximately 270° C. to approximately 400° C. In some embodiments, the sheath gas heater setting is approximately 270° C. to approximately 395° C. In some embodiments, the sheath gas heater setting is approximately 270° C. to approximately 390° C. In some embodiments, the sheath gas heater setting is approximately 270° C. to approximately 385° C. In some embodiments, the sheath gas heater setting is approximately 270° C. to approximately 380° C. In some embodiments, the sheath gas heater setting is approximately 270° C. to approximately 375° C. In some embodiments, the sheath gas heater setting is approximately 270° C. to approximately 370° C. In some embodiments, the sheath gas heater setting is approximately 270° C. to approximately 365° C. In some embodiments, the sheath gas heater setting is approximately 270° C. to approximately 360° C. In some embodiments, the sheath gas heater setting is approximately 270° C. to approximately 355° C. In some embodiments, the sheath gas heater setting is approximately 270° C. to approximately 350° C. In some embodiments, the sheath gas heater setting is approximately 270° C. to approximately 345° C. In some embodiments, the sheath gas heater setting is approximately 270° C. to approximately 340° C. In some embodiments, the sheath gas heater setting is approximately 270° C. to approximately 335° C. In some embodiments, the sheath gas heater setting is approximately 270° C. to approximately 330° C. In some embodiments, the sheath gas heater setting is approximately 270° C. to approximately 325° C. In some embodiments, the sheath gas heater setting is approximately 270° C. to approximately 320° C. In some embodiments, the sheath gas heater setting is approximately 270° C. to approximately 315° C. In some embodiments, the sheath gas heater setting is approximately 270° C. to approximately 310° C. In some embodiments, the sheath gas heater setting is approximately 270° C. to approximately 305° C. In some embodiments, the sheath gas heater setting is approximately 270° C. to approximately 300° C. In some embodiments, the sheath gas heater setting is approximately 270° C. to approximately 295° C. In some embodiments, the sheath gas heater setting is approximately 270° C. to approximately 290° C. In some embodiments, the sheath gas heater setting is approximately 270° C. to approximately 285° C. In some embodiments, the sheath gas heater setting is approximately 270° C. to approximately 280° C. In some embodiments, the sheath gas heater setting is approximately 270° C. to approximately 275° C. In some embodiments, the sheath gas heater setting is approximately 270° C.

In various embodiments, ESI conditions include a sheath gas heater setting of approximately 275° C. to approximately 400° C. In some embodiments, the sheath gas heater setting is approximately 275° C. to approximately 395° C. In some embodiments, the sheath gas heater setting is approximately 275° C. to approximately 390° C. In some embodiments, the sheath gas heater setting is approximately 275° C. to approximately 385° C. In some embodiments, the sheath gas heater setting is approximately 275° C. to approximately 380° C. In some embodiments, the sheath gas heater setting is approximately 275° C. to approximately 375° C. In some embodiments, the sheath gas heater setting is approximately 275° C. to approximately 370° C. In some embodiments, the sheath gas heater setting is approximately 275° C. to approximately 365° C. In some embodiments, the sheath gas heater setting is approximately 275° C. to approximately 360° C. In some embodiments, the sheath gas heater setting is approximately 275° C. to approximately 355° C. In some embodiments, the sheath gas heater setting is approximately 275° C. to approximately 350° C. In some embodiments, the sheath gas heater setting is approximately 275° C. to approximately 345° C. In some embodiments, the sheath gas heater setting is approximately 275° C. to approximately 340° C. In some embodiments, the sheath gas heater setting is approximately 275° C. to approximately 335° C. In some embodiments, the sheath gas heater setting is approximately 275° C. to approximately 330° C. In some embodiments, the sheath gas heater setting is approximately 275° C. to approximately 325° C. In some embodiments, the sheath gas heater setting is approximately 275° C. to approximately 320° C. In some embodiments, the sheath gas heater setting is approximately 275° C. to approximately 315° C. In some embodiments, the sheath gas heater setting is approximately 275° C. to approximately 310° C. In some embodiments, the sheath gas heater setting is approximately 275° C. to approximately 305° C. In some embodiments, the sheath gas heater setting is approximately 275° C. to approximately 300° C. In some embodiments, the sheath gas heater setting is approximately 275° C. to approximately 295° C. In some embodiments, the sheath gas heater setting is approximately 275° C. to approximately 290° C. In some embodiments, the sheath gas heater setting is approximately 275° C. to approximately 285° C. In some embodiments, the sheath gas heater setting is approximately 275° C. to approximately 280° C. In some embodiments, the sheath gas heater setting is approximately 275° C.

In various embodiments, ESI conditions include a sheath gas heater setting of approximately 280° C. to approximately 400° C. In some embodiments, the sheath gas heater setting is approximately 280° C. to approximately 395° C. In some embodiments, the sheath gas heater setting is approximately 280° C. to approximately 390° C. In some embodiments, the sheath gas heater setting is approximately 280° C. to approximately 385° C. In some embodiments, the sheath gas heater setting is approximately 280° C. to approximately 380° C. In some embodiments, the sheath gas heater setting is approximately 280° C. to approximately 375° C. In some embodiments, the sheath gas heater setting is approximately 280° C. to approximately 370° C. In some embodiments, the sheath gas heater setting is approximately 280° C. to approximately 365° C. In some embodiments, the sheath gas heater setting is approximately 280° C. to approximately 360° C. In some embodiments, the sheath gas heater setting is approximately 280° C. to approximately 355° C. In some embodiments, the sheath gas heater setting is approximately 280° C. to approximately 350° C. In some embodiments, the sheath gas heater setting is approximately 280° C. to approximately 345° C. In some embodiments, the sheath gas heater setting is approximately 280° C. to approximately 340° C. In some embodiments, the sheath gas heater setting is approximately 280° C. to approximately 335° C. In some embodiments, the sheath gas heater setting is approximately 280° C. to approximately 330° C. In some embodiments, the sheath gas heater setting is approximately 280° C. to approximately 325° C. In some embodiments, the sheath gas heater setting is approximately 280° C. to approximately 320° C. In some embodiments, the sheath gas heater setting is approximately 280° C. to approximately 315° C. In some embodiments, the sheath gas heater setting is approximately 280° C. to approximately 310° C. In some embodiments, the sheath gas heater setting is approximately 280° C. to approximately 305° C. In some embodiments, the sheath gas heater setting is approximately 280° C. to approximately 300° C. In some embodiments, the sheath gas heater setting is approximately 280° C. to approximately 295° C. In some embodiments, the sheath gas heater setting is approximately 280° C. to approximately 290° C. In some embodiments, the sheath gas heater setting is approximately 280° C. to approximately 285° C. In some embodiments, the sheath gas heater setting is approximately 280° C.

In various embodiments, ESI conditions include a sheath gas heater setting of approximately 285° C. to approximately 400° C. In some embodiments, the sheath gas heater setting is approximately 285° C. to approximately 395° C. In some embodiments, the sheath gas heater setting is approximately 285° C. to approximately 390° C. In some embodiments, the sheath gas heater setting is approximately 285° C. to approximately 385° C. In some embodiments, the sheath gas heater setting is approximately 285° C. to approximately 380° C. In some embodiments, the sheath gas heater setting is approximately 285° C. to approximately 375° C. In some embodiments, the sheath gas heater setting is approximately 285° C. to approximately 370° C. In some embodiments, the sheath gas heater setting is approximately 285° C. to approximately 365° C. In some embodiments, the sheath gas heater setting is approximately 285° C. to approximately 360° C. In some embodiments, the sheath gas heater setting is approximately 285° C. to approximately 355° C. In some embodiments, the sheath gas heater setting is approximately 285° C. to approximately 350° C. In some embodiments, the sheath gas heater setting is approximately 285° C. to approximately 345° C. In some embodiments, the sheath gas heater setting is approximately 285° C. to approximately 340° C. In some embodiments, the sheath gas heater setting is approximately 285° C. to approximately 335° C. In some embodiments, the sheath gas heater setting is approximately 285° C. to approximately 330° C. In some embodiments, the sheath gas heater setting is approximately 285° C. to approximately 325° C. In some embodiments, the sheath gas heater setting is approximately 285° C. to approximately 320° C. In some embodiments, the sheath gas heater setting is approximately 285° C. to approximately 315° C. In some embodiments, the sheath gas heater setting is approximately 285° C. to approximately 310° C. In some embodiments, the sheath gas heater setting is approximately 285° C. to approximately 305° C. In some embodiments, the sheath gas heater setting is approximately 285° C. to approximately 300° C. In some embodiments, the sheath gas heater setting is approximately 285° C. to approximately 295° C. In some embodiments, the sheath gas heater setting is approximately 285° C. to approximately 290° C. In some embodiments, the sheath gas heater setting is approximately 285° C.

In various embodiments, ESI conditions include a sheath gas heater setting of approximately 290° C. to approximately 400° C. In some embodiments, the sheath gas heater setting is approximately 290° C. to approximately 395° C. In some embodiments, the sheath gas heater setting is approximately 290° C. to approximately 390° C. In some embodiments, the sheath gas heater setting is approximately 290° C. to approximately 385° C. In some embodiments, the sheath gas heater setting is approximately 290° C. to approximately 380° C. In some embodiments, the sheath gas heater setting is approximately 290° C. to approximately 375° C. In some embodiments, the sheath gas heater setting is approximately 290° C. to approximately 370° C. In some embodiments, the sheath gas heater setting is approximately 290° C. to approximately 365° C. In some embodiments, the sheath gas heater setting is approximately 290° C. to approximately 360° C. In some embodiments, the sheath gas heater setting is approximately 290° C. to approximately 355° C. In some embodiments, the sheath gas heater setting is approximately 290° C. to approximately 350° C. In some embodiments, the sheath gas heater setting is approximately 290° C. to approximately 345° C. In some embodiments, the sheath gas heater setting is approximately 290° C. to approximately 340° C. In some embodiments, the sheath gas heater setting is approximately 290° C. to approximately 335° C. In some embodiments, the sheath gas heater setting is approximately 290° C. to approximately 330° C. In some embodiments, the sheath gas heater setting is approximately 290° C. to approximately 325° C. In some embodiments, the sheath gas heater setting is approximately 290° C. to approximately 320° C. In some embodiments, the sheath gas heater setting is approximately 290° C. to approximately 315° C. In some embodiments, the sheath gas heater setting is approximately 290° C. to approximately 310° C. In some embodiments, the sheath gas heater setting is approximately 290° C. to approximately 305° C. In some embodiments, the sheath gas heater setting is approximately 290° C. to approximately 300° C. In some embodiments, the sheath gas heater setting is approximately 290° C. to approximately 295° C. In some embodiments, the sheath gas heater setting is approximately 290° C.

In various embodiments, ESI conditions include a sheath gas heater setting of approximately 295° C. to approximately 400° C. In some embodiments, the sheath gas heater setting is approximately 295° C. to approximately 395° C. In some embodiments, the sheath gas heater setting is approximately 295° C. to approximately 390° C. In some embodiments, the sheath gas heater setting is approximately 295° C. to approximately 385° C. In some embodiments, the sheath gas heater setting is approximately 295° C. to approximately 380° C. In some embodiments, the sheath gas heater setting is approximately 295° C. to approximately 375° C. In some embodiments, the sheath gas heater setting is approximately 295° C. to approximately 370° C. In some embodiments, the sheath gas heater setting is approximately 295° C. to approximately 365° C. In some embodiments, the sheath gas heater setting is approximately 295° C. to approximately 360° C. In some embodiments, the sheath gas heater setting is approximately 295° C. to approximately 355° C. In some embodiments, the sheath gas heater setting is approximately 295° C. to approximately 350° C. In some embodiments, the sheath gas heater setting is approximately 295° C. to approximately 345° C. In some embodiments, the sheath gas heater setting is approximately 295° C. to approximately 340° C. In some embodiments, the sheath gas heater setting is approximately 295° C. to approximately 335° C. In some embodiments, the sheath gas heater setting is approximately 295° C. to approximately 330° C. In some embodiments, the sheath gas heater setting is approximately 295° C. to approximately 325° C. In some embodiments, the sheath gas heater setting is approximately 295° C. to approximately 320° C. In some embodiments, the sheath gas heater setting is approximately 295° C. to approximately 315° C. In some embodiments, the sheath gas heater setting is approximately 295° C. to approximately 310° C. In some embodiments, the sheath gas heater setting is approximately 295° C. to approximately 305° C. In some embodiments, the sheath gas heater setting is approximately 295° C. to approximately 300° C. In some embodiments, the sheath gas heater setting is approximately 295° C.

In various embodiments, ESI conditions include a sheath gas heater setting of approximately 300° C. to approximately 400° C. In some embodiments, the sheath gas heater setting is approximately 300° C. to approximately 395° C. In some embodiments, the sheath gas heater setting is approximately 300° C. to approximately 390° C. In some embodiments, the sheath gas heater setting is approximately 300° C. to approximately 385° C. In some embodiments, the sheath gas heater setting is approximately 300° C. to approximately 380° C. In some embodiments, the sheath gas heater setting is approximately 300° C. to approximately 375° C. In some embodiments, the sheath gas heater setting is approximately 300° C. to approximately 370° C. In some embodiments, the sheath gas heater setting is approximately 300° C. to approximately 365° C. In some embodiments, the sheath gas heater setting is approximately 300° C. to approximately 360° C. In some embodiments, the sheath gas heater setting is approximately 300° C. to approximately 355° C. In some embodiments, the sheath gas heater setting is approximately 300° C. to approximately 350° C. In some embodiments, the sheath gas heater setting is approximately 300° C. to approximately 345° C. In some embodiments, the sheath gas heater setting is approximately 300° C. to approximately 340° C. In some embodiments, the sheath gas heater setting is approximately 300° C. to approximately 335° C. In some embodiments, the sheath gas heater setting is approximately 300° C. to approximately 330° C. In some embodiments, the sheath gas heater setting is approximately 300° C. to approximately 325° C. In some embodiments, the sheath gas heater setting is approximately 300° C. to approximately 320° C. In some embodiments, the sheath gas heater setting is approximately 300° C. to approximately 315° C. In some embodiments, the sheath gas heater setting is approximately 300° C. to approximately 310° C. In some embodiments, the sheath gas heater setting is approximately 300° C. to approximately 305° C. In some embodiments, the sheath gas heater setting is approximately 300° C.

In various embodiments, ESI conditions include a sheath gas heater setting of approximately 305° C. to approximately 400° C. In some embodiments, the sheath gas heater setting is approximately 305° C. to approximately 395° C. In some embodiments, the sheath gas heater setting is approximately 305° C. to approximately 390° C. In some embodiments, the sheath gas heater setting is approximately 305° C. to approximately 385° C. In some embodiments, the sheath gas heater setting is approximately 305° C. to approximately 380° C. In some embodiments, the sheath gas heater setting is approximately 305° C. to approximately 375° C. In some embodiments, the sheath gas heater setting is approximately 305° C. to approximately 370° C. In some embodiments, the sheath gas heater setting is approximately 305° C. to approximately 365° C. In some embodiments, the sheath gas heater setting is approximately 305° C. to approximately 360° C. In some embodiments, the sheath gas heater setting is approximately 305° C. to approximately 355° C. In some embodiments, the sheath gas heater setting is approximately 305° C. to approximately 350° C. In some embodiments, the sheath gas heater setting is approximately 305° C. to approximately 345° C. In some embodiments, the sheath gas heater setting is approximately 305° C. to approximately 340° C. In some embodiments, the sheath gas heater setting is approximately 305° C. to approximately 335° C. In some embodiments, the sheath gas heater setting is approximately 305° C. to approximately 330° C. In some embodiments, the sheath gas heater setting is approximately 305° C. to approximately 325° C. In some embodiments, the sheath gas heater setting is approximately 305° C. to approximately 320° C. In some embodiments, the sheath gas heater setting is approximately 305° C. to approximately 315° C. In some embodiments, the sheath gas heater setting is approximately 305° C. to approximately 310° C. In some embodiments, the sheath gas heater setting is approximately 305° C.

In various embodiments, ESI conditions include a sheath gas heater setting of approximately 310° C. to approximately 400° C. In some embodiments, the sheath gas heater setting is approximately 310° C. to approximately 395° C. In some embodiments, the sheath gas heater setting is approximately 310° C. to approximately 390° C. In some embodiments, the sheath gas heater setting is approximately 310° C. to approximately 385° C. In some embodiments, the sheath gas heater setting is approximately 310° C. to approximately 380° C. In some embodiments, the sheath gas heater setting is approximately 310° C. to approximately 375° C. In some embodiments, the sheath gas heater setting is approximately 310° C. to approximately 370° C. In some embodiments, the sheath gas heater setting is approximately 310° C. to approximately 365° C. In some embodiments, the sheath gas heater setting is approximately 310° C. to approximately 360° C. In some embodiments, the sheath gas heater setting is approximately 310° C. to approximately 355° C. In some embodiments, the sheath gas heater setting is approximately 310° C. to approximately 350° C. In some embodiments, the sheath gas heater setting is approximately 310° C. to approximately 345° C. In some embodiments, the sheath gas heater setting is approximately 310° C. to approximately 340° C. In some embodiments, the sheath gas heater setting is approximately 310° C. to approximately 335° C. In some embodiments, the sheath gas heater setting is approximately 310° C. to approximately 330° C. In some embodiments, the sheath gas heater setting is approximately 310° C. to approximately 325° C. In some embodiments, the sheath gas heater setting is approximately 310° C. to approximately 320° C. In some embodiments, the sheath gas heater setting is approximately 310° C. to approximately 315° C. In some embodiments, the sheath gas heater setting is approximately 310° C.

In various embodiments, ESI conditions include a sheath gas heater setting of approximately 315° C. to approximately 400° C. In some embodiments, the sheath gas heater setting is approximately 315° C. to approximately 395° C. In some embodiments, the sheath gas heater setting is approximately 315° C. to approximately 390° C. In some embodiments, the sheath gas heater setting is approximately 315° C. to approximately 385° C. In some embodiments, the sheath gas heater setting is approximately 315° C. to approximately 380° C. In some embodiments, the sheath gas heater setting is approximately 315° C. to approximately 375° C. In some embodiments, the sheath gas heater setting is approximately 315° C. to approximately 370° C. In some embodiments, the sheath gas heater setting is approximately 315° C. to approximately 365° C. In some embodiments, the sheath gas heater setting is approximately 315° C. to approximately 360° C. In some embodiments, the sheath gas heater setting is approximately 315° C. to approximately 355° C. In some embodiments, the sheath gas heater setting is approximately 315° C. to approximately 350° C. In some embodiments, the sheath gas heater setting is approximately 315° C. to approximately 345° C. In some embodiments, the sheath gas heater setting is approximately 315° C. to approximately 340° C. In some embodiments, the sheath gas heater setting is approximately 315° C. to approximately 335° C. In some embodiments, the sheath gas heater setting is approximately 315° C. to approximately 330° C. In some embodiments, the sheath gas heater setting is approximately 315° C. to approximately 325° C. In some embodiments, the sheath gas heater setting is approximately 315° C. to approximately 320° C. In some embodiments, the sheath gas heater setting is approximately 315° C.

In various embodiments, ESI conditions include a sheath gas heater setting of approximately 320° C. to approximately 400° C. In some embodiments, the sheath gas heater setting is approximately 320° C. to approximately 395° C. In some embodiments, the sheath gas heater setting is approximately 320° C. to approximately 390° C. In some embodiments, the sheath gas heater setting is approximately 320° C. to approximately 385° C. In some embodiments, the sheath gas heater setting is approximately 320° C. to approximately 380° C. In some embodiments, the sheath gas heater setting is approximately 320° C. to approximately 375° C. In some embodiments, the sheath gas heater setting is approximately 320° C. to approximately 370° C. In some embodiments, the sheath gas heater setting is approximately 320° C. to approximately 365° C. In some embodiments, the sheath gas heater setting is approximately 320° C. to approximately 360° C. In some embodiments, the sheath gas heater setting is approximately 320° C. to approximately 355° C. In some embodiments, the sheath gas heater setting is approximately 320° C. to approximately 350° C. In some embodiments, the sheath gas heater setting is approximately 320° C. to approximately 345° C. In some embodiments, the sheath gas heater setting is approximately 320° C. to approximately 340° C. In some embodiments, the sheath gas heater setting is approximately 320° C. to approximately 335° C. In some embodiments, the sheath gas heater setting is approximately 320° C. to approximately 330° C. In some embodiments, the sheath gas heater setting is approximately 320° C. to approximately 325° C. In some embodiments, the sheath gas heater setting is approximately 320° C.

In various embodiments, ESI conditions include a sheath gas heater setting of approximately 325° C. to approximately 400° C. In some embodiments, the sheath gas heater setting is approximately 325° C. to approximately 395° C. In some embodiments, the sheath gas heater setting is approximately 325° C. to approximately 390° C. In some embodiments, the sheath gas heater setting is approximately 325° C. to approximately 385° C. In some embodiments, the sheath gas heater setting is approximately 325° C. to approximately 380° C. In some embodiments, the sheath gas heater setting is approximately 325° C. to approximately 375° C. In some embodiments, the sheath gas heater setting is approximately 325° C. to approximately 370° C. In some embodiments, the sheath gas heater setting is approximately 325° C. to approximately 365° C. In some embodiments, the sheath gas heater setting is approximately 325° C. to approximately 360° C. In some embodiments, the sheath gas heater setting is approximately 325° C. to approximately 355° C. In some embodiments, the sheath gas heater setting is approximately 325° C. to approximately 350° C. In some embodiments, the sheath gas heater setting is approximately 325° C. to approximately 345° C. In some embodiments, the sheath gas heater setting is approximately 325° C. to approximately 340° C. In some embodiments, the sheath gas heater setting is approximately 325° C. to approximately 335° C. In some embodiments, the sheath gas heater setting is approximately 325° C. to approximately 330° C. In some embodiments, the sheath gas heater setting is approximately 325° C.

In various embodiments, ESI conditions include a sheath gas heater setting of approximately 330° C. to approximately 400° C. In some embodiments, the sheath gas heater setting is approximately 330° C. to approximately 395° C. In some embodiments, the sheath gas heater setting is approximately 330° C. to approximately 390° C. In some embodiments, the sheath gas heater setting is approximately 330° C. to approximately 385° C. In some embodiments, the sheath gas heater setting is approximately 330° C. to approximately 380° C. In some embodiments, the sheath gas heater setting is approximately 330° C. to approximately 375° C. In some embodiments, the sheath gas heater setting is approximately 330° C. to approximately 370° C. In some embodiments, the sheath gas heater setting is approximately 330° C. to approximately 365° C. In some embodiments, the sheath gas heater setting is approximately 330° C. to approximately 360° C. In some embodiments, the sheath gas heater setting is approximately 330° C. to approximately 355° C. In some embodiments, the sheath gas heater setting is approximately 330° C. to approximately 350° C. In some embodiments, the sheath gas heater setting is approximately 330° C. to approximately 345° C. In some embodiments, the sheath gas heater setting is approximately 330° C. to approximately 340° C. In some embodiments, the sheath gas heater setting is approximately 330° C. to approximately 335° C. In some embodiments, the sheath gas heater setting is approximately 330° C.

In various embodiments, ESI conditions include a sheath gas heater setting of approximately 335° C. to approximately 400° C. In some embodiments, the sheath gas heater setting is approximately 335° C. to approximately 395° C. In some embodiments, the sheath gas heater setting is approximately 335° C. to approximately 390° C. In some embodiments, the sheath gas heater setting is approximately 335° C. to approximately 385° C. In some embodiments, the sheath gas heater setting is approximately 335° C. to approximately 380° C. In some embodiments, the sheath gas heater setting is approximately 335° C. to approximately 375° C. In some embodiments, the sheath gas heater setting is approximately 335° C. to approximately 370° C. In some embodiments, the sheath gas heater setting is approximately 335° C. to approximately 365° C. In some embodiments, the sheath gas heater setting is approximately 335° C. to approximately 360° C. In some embodiments, the sheath gas heater setting is approximately 335° C. to approximately 355° C. In some embodiments, the sheath gas heater setting is approximately 335° C. to approximately 350° C. In some embodiments, the sheath gas heater setting is approximately 335° C. to approximately 345° C. In some embodiments, the sheath gas heater setting is approximately 335° C. to approximately 340° C. In some embodiments, the sheath gas heater setting is approximately 335° C.

In various embodiments, ESI conditions include a sheath gas heater setting of approximately 340° C. to approximately 400° C. In some embodiments, the sheath gas heater setting is approximately 340° C. to approximately 395° C. In some embodiments, the sheath gas heater setting is approximately 340° C. to approximately 390° C. In some embodiments, the sheath gas heater setting is approximately 340° C. to approximately 385° C. In some embodiments, the sheath gas heater setting is approximately 340° C. to approximately 380° C. In some embodiments, the sheath gas heater setting is approximately 340° C. to approximately 375° C. In some embodiments, the sheath gas heater setting is approximately 340° C. to approximately 370° C. In some embodiments, the sheath gas heater setting is approximately 340° C. to approximately 365° C. In some embodiments, the sheath gas heater setting is approximately 340° C. to approximately 360° C. In some embodiments, the sheath gas heater setting is approximately 340° C. to approximately 355° C. In some embodiments, the sheath gas heater setting is approximately 340° C. to approximately 350° C. In some embodiments, the sheath gas heater setting is approximately 340° C. to approximately 345° C. In some embodiments, the sheath gas heater setting is approximately 340° C.

In various embodiments, ESI conditions include a sheath gas heater setting of approximately 345° C. to approximately 400° C. In some embodiments, the sheath gas heater setting is approximately 345° C. to approximately 395° C. In some embodiments, the sheath gas heater setting is approximately 345° C. to approximately 390° C. In some embodiments, the sheath gas heater setting is approximately 345° C. to approximately 385° C. In some embodiments, the sheath gas heater setting is approximately 345° C. to approximately 380° C. In some embodiments, the sheath gas heater setting is approximately 345° C. to approximately 375° C. In some embodiments, the sheath gas heater setting is approximately 345° C. to approximately 370° C. In some embodiments, the sheath gas heater setting is approximately 345° C. to approximately 365° C. In some embodiments, the sheath gas heater setting is approximately 345° C. to approximately 360° C. In some embodiments, the sheath gas heater setting is approximately 345° C. to approximately 355° C. In some embodiments, the sheath gas heater setting is approximately 345° C. to approximately 350° C. In some embodiments, the sheath gas heater setting is approximately 345° C.

In various embodiments, ESI conditions include a sheath gas heater setting of approximately 350° C. to approximately 400° C. In some embodiments, the sheath gas heater setting is approximately 350° C. to approximately 395° C. In some embodiments, the sheath gas heater setting is approximately 350° C. to approximately 390° C. In some embodiments, the sheath gas heater setting is approximately 350° C. to approximately 385° C. In some embodiments, the sheath gas heater setting is approximately 350° C. to approximately 380° C. In some embodiments, the sheath gas heater setting is approximately 350° C. to approximately 375° C. In some embodiments, the sheath gas heater setting is approximately 350° C. to approximately 370° C. In some embodiments, the sheath gas heater setting is approximately 350° C. to approximately 365° C. In some embodiments, the sheath gas heater setting is approximately 350° C. to approximately 360° C. In some embodiments, the sheath gas heater setting is approximately 350° C. to approximately 355° C. In some embodiments, the sheath gas heater setting is approximately 350° C.

In various embodiments, ESI conditions include a sheath gas heater setting of approximately 355° C. to approximately 400° C. In some embodiments, the sheath gas heater setting is approximately 355° C. to approximately 395° C. In some embodiments, the sheath gas heater setting is approximately 355° C. to approximately 390° C. In some embodiments, the sheath gas heater setting is approximately 355° C. to approximately 385° C. In some embodiments, the sheath gas heater setting is approximately 355° C. to approximately 380° C. In some embodiments, the sheath gas heater setting is approximately 355° C. to approximately 375° C. In some embodiments, the sheath gas heater setting is approximately 355° C. to approximately 370° C. In some embodiments, the sheath gas heater setting is approximately 355° C. to approximately 365° C. In some embodiments, the sheath gas heater setting is approximately 355° C. to approximately 360° C. In some embodiments, the sheath gas heater setting is approximately 355° C.

In various embodiments, ESI conditions include a sheath gas heater setting of approximately 360° C. to approximately 400° C. In some embodiments, the sheath gas heater setting is approximately 360° C. to approximately 395° C. In some embodiments, the sheath gas heater setting is approximately 360° C. to approximately 390° C. In some embodiments, the sheath gas heater setting is approximately 360° C. to approximately 385° C. In some embodiments, the sheath gas heater setting is approximately 360° C. to approximately 380° C. In some embodiments, the sheath gas heater setting is approximately 360° C. to approximately 375° C. In some embodiments, the sheath gas heater setting is approximately 360° C. to approximately 370° C. In some embodiments, the sheath gas heater setting is approximately 360° C. to approximately 365° C. In some embodiments, the sheath gas heater setting is approximately 360° C.

In various embodiments, ESI conditions include a sheath gas heater setting of approximately 365° C. to approximately 400° C. In some embodiments, the sheath gas heater setting is approximately 365° C. to approximately 395° C. In some embodiments, the sheath gas heater setting is approximately 365° C. to approximately 390° C. In some embodiments, the sheath gas heater setting is approximately 365° C. to approximately 385° C. In some embodiments, the sheath gas heater setting is approximately 365° C. to approximately 380° C. In some embodiments, the sheath gas heater setting is approximately 365° C. to approximately 375° C. In some embodiments, the sheath gas heater setting is approximately 365° C. to approximately 370° C. In some embodiments, the sheath gas heater setting is approximately 365° C.

In various embodiments, ESI conditions include a sheath gas heater setting of approximately 370° C. to approximately 400° C. In some embodiments, the sheath gas heater setting is approximately 370° C. to approximately 395° C. In some embodiments, the sheath gas heater setting is approximately 370° C. to approximately 390° C. In some embodiments, the sheath gas heater setting is approximately 370° C. to approximately 385° C. In some embodiments, the sheath gas heater setting is approximately 370° C. to approximately 380° C. In some embodiments, the sheath gas heater setting is approximately 370° C. to approximately 375° C. In some embodiments, the sheath gas heater setting is approximately 370° C.

In various embodiments, ESI conditions include a sheath gas heater setting of approximately 375° C. to approximately 400° C. In some embodiments, the sheath gas heater setting is approximately 375° C. to approximately 395° C. In some embodiments, the sheath gas heater setting is approximately 375° C. to approximately 390° C. In some embodiments, the sheath gas heater setting is approximately 375° C. to approximately 385° C. In some embodiments, the sheath gas heater setting is approximately 375° C. to approximately 380° C. In some embodiments, the sheath gas heater setting is approximately 375° C.

In various embodiments, ESI conditions include a sheath gas heater setting of approximately 380° C. to approximately 400° C. In some embodiments, the sheath gas heater setting is approximately 380° C. to approximately 395° C. In some embodiments, the sheath gas heater setting is approximately 380° C. to approximately 390° C. In some embodiments, the sheath gas heater setting is approximately 380° C. to approximately 385° C. In some embodiments, the sheath gas heater setting is approximately 380° C.

In various embodiments, ESI conditions include a sheath gas heater setting of approximately 385° C. to approximately 400° C. In some embodiments, the sheath gas heater setting is approximately 385° C. to approximately 395° C. In some embodiments, the sheath gas heater setting is approximately 385° C. to approximately 390° C. In some embodiments, the sheath gas heater setting is approximately 385° C.

In various embodiments, ESI conditions include a sheath gas heater setting of approximately 390° C. to approximately 400° C. In some embodiments, the sheath gas heater setting is approximately 390° C. to approximately 395° C. In some embodiments, the sheath gas heater setting is approximately 390° C.

In various embodiments, ESI conditions include a sheath gas heater setting of approximately 395° C. to approximately 400° C. In some embodiments, the sheath gas heater setting is approximately 395° C. In some embodiments, the sheath gas heater setting is approximately 400° C.

In some embodiments when the PFAS analyte solution includes PFBA as analyte, the sheath gas heater setting ranges from approximately 250° C. to approximately 400° C. In some embodiments when the PFAS analyte solution includes PFBA as analyte, the sheath gas heater setting is approximately 400° C.

In some embodiments when the PFAS analyte solution contains PFBS as analyte, the sheath gas heater setting ranges from approximately 300° C. to approximately 400° C. In some embodiments when the PFAS analyte solution includes PFBS as analyte, the sheath gas heater setting is approximately 400° C.

In some embodiments when the PFAS analyte solution contains PFHpA as analyte, the sheath gas heater setting ranges from approximately 275° C. to approximately 400° C. In some embodiments when the PFAS analyte solution includes PFHpA as analyte, the sheath gas heater setting is approximately 400° C.

In some embodiments when the PFAS analyte solution contains PFHxA as analyte, the sheath gas heater setting ranges from approximately 300° C. to approximately 400° C. In some embodiments when the PFAS analyte solution includes PFHxA as analyte, the sheath gas heater setting is approximately 400° C.

In some embodiments when the PFAS analyte solution contains PFHxS as analyte, the sheath gas heater setting ranges from approximately 300° C. to approximately 400° C. In some embodiments when the PFAS analyte solution includes PFHxS as analyte, the sheath gas heater setting is approximately 400° C.

In some embodiments when the PFAS analyte solution contains PFPeS as analyte, the sheath gas heater setting ranges from approximately 300° C. to approximately 400° C. In some embodiments when the PFAS analyte solution includes PFPeS as analyte, the sheath gas heater setting is approximately 400° C.

In some embodiments when the PFAS analyte solution contains PFDA as analyte, the sheath gas heater setting ranges from approximately 275° C. to approximately 400° C. In some embodiments when the PFAS analyte solution includes PFDA as analyte, the sheath gas heater setting is approximately 400° C.

In some embodiments when the PFAS analyte solution contains PFHpS as analyte, the sheath gas heater setting ranges from approximately 300° C. to approximately 400° C. In some embodiments when the PFAS analyte solution includes PFHpS as analyte, the sheath gas heater setting is approximately 400° C.

In some embodiments when the PFAS analyte solution contains PFOS as analyte, the sheath gas heater setting ranges from approximately 350° C. to approximately 400° C. In some embodiments when the PFAS analyte solution includes PFOS as analyte, the sheath gas heater setting is approximately 400° C.

In some embodiments when the PFAS analyte solution contains PFNA as analyte, the sheath gas heater setting ranges from approximately 300° C. to approximately 400° C. In some embodiments when the PFAS analyte solution includes PFNA as analyte, the sheath gas heater setting is approximately 400° C.

In some embodiments when the PFAS analyte solution contains PFNS as analyte, the sheath gas heater setting ranges from approximately 300° C. to approximately 400° C. In some embodiments when the PFAS analyte solution includes PFNS as analyte, the sheath gas heater setting is approximately 400° C.

In some embodiments when the PFAS analyte solution contains PFOA as analyte, the sheath gas heater setting ranges from approximately 300° C. to approximately 400° C. In some embodiments when the PFAS analyte solution includes PFOA as analyte, the sheath gas heater setting is approximately 400° C.

In some embodiments, the ESI sheath gas heater setting is set on an AGILENT 6490 or 6495 mass spectrometer. In exemplary embodiments, the ESI sheath gas heater setting is set on an AGILENT 6495 mass spectrometer.

In various embodiments, ESI conditions include a sheath gas flow ("Sheath Gas Flow") of approximately 8 L/min to approximately 12 L/min. In some embodiments, the sheath gas flow is approximately 8 L/min to approximately 11 L/min. In some embodiments, the sheath gas flow is approximately 8 L/min to approximately 10 L/min. In some embodiments, the sheath gas flow is approximately 8 L/min to approximately 9 L/min. In some embodiments, the sheath gas flow is approximately 8 L/min.

In various embodiments, ESI conditions include a sheath gas flow of approximately 9 L/min to approximately 12 L/min. In some embodiments, the sheath gas flow is approximately 9 L/min to approximately 11 L/min. In some embodiments, the sheath gas flow is approximately 9 L/min to approximately 10 L/min. In some embodiments, the sheath gas flow is approximately 9 L/min.

In various embodiments, ESI conditions include a sheath gas flow of approximately 10 L/min to approximately 12 L/min. In some embodiments, the sheath gas flow is approximately 10 L/min to approximately 11 L/min. In some embodiments, the sheath gas flow is approximately 10 L/min.

In various embodiments, ESI conditions include a sheath gas flow of approximately 11 L/min to approximately 12 L/min. In some embodiments, the sheath gas flow is approximately 11 L/min. In some embodiments, the sheath gas flow is approximately 12 L/min.

In some embodiments when the PFAS analyte solution includes PFBA as analyte, the sheath gas flow setting ranges from approximately 8 L/min to approximately 12 L/min. In some embodiments when the PFAS analyte solution includes PFBA as analyte, the sheath gas flow setting is approximately 8 L/min.

In some embodiments when the PFAS analyte solution contains PFBS as analyte, the sheath gas flow setting ranges from approximately 8 L/min to approximately 12 L/min. In some embodiments when the PFAS analyte solution contains PFBS as analyte, the sheath gas flow setting is approximately 8 L/min.

In some embodiments when the PFAS analyte solution contains PFHpA as analyte, the sheath gas flow setting ranges from approximately 8 L/min to approximately 10 L/min. In some embodiments when the PFAS analyte solution contains PFHpA as analyte, the sheath gas flow setting is approximately 8 L/min.

In some embodiments when the PFAS analyte solution contains PFHxA as analyte, the sheath gas flow setting ranges from approximately 8 L/min to approximately 10 L/min. In some embodiments when the PFAS analyte solution contains PFHxA as analyte, the sheath gas flow setting is approximately 8 L/min.

In some embodiments when the PFAS analyte solution contains PFHxS as analyte, the sheath gas flow setting ranges from approximately 8 L/min to approximately 12 L/min. In some embodiments when the PFAS analyte solution contains PFHxS as analyte, the sheath gas flow setting is approximately 8 L/min.

In some embodiments when the PFAS analyte solution contains PFPeS as analyte, the sheath gas flow setting ranges from approximately 8 L/min to approximately 12 L/min. In some embodiments when the PFAS analyte solution contains PFPeS as analyte, the sheath gas flow setting is approximately 8 L/min.

In some embodiments when the PFAS analyte solution contains PFDA as analyte, the sheath gas flow setting ranges from approximately 8 L/min to approximately 9 L/min. In some embodiments when the PFAS analyte solution contains PFDA as analyte, the sheath gas flow setting is approximately 8 L/min.

In some embodiments when the PFAS analyte solution contains PFHpS as analyte, the sheath gas flow setting ranges from approximately 8 L/min to approximately 12 L/min. In some embodiments when the PFAS analyte solution contains PFHpS as analyte, the sheath gas flow setting is approximately 8 L/min.

In some embodiments when the PFAS analyte solution contains PFOS as analyte, the sheath gas flow setting ranges from approximately 8 L/min to approximately 9 L/min. In some embodiments when the PFAS analyte solution contains PFOS as analyte, the sheath gas flow setting is approximately 8 L/min.

In some embodiments when the PFAS analyte solution contains PFNA as analyte, the sheath gas flow setting ranges from approximately 8 L/min to approximately 9 L/min. In some embodiments when the PFAS analyte solution contains PFNA as analyte, the sheath gas flow setting is approximately 8 L/min.

In some embodiments when the PFAS analyte solution contains PFNS as analyte, the sheath gas flow setting ranges from approximately 8 L/min to approximately 12 L/min. In some embodiments when the PFAS analyte solution contains PFNS as analyte, the sheath gas flow setting is approximately 8 L/min.

In some embodiments when the PFAS analyte solution contains PFOA as analyte, the sheath gas flow setting ranges from approximately 8 L/min to approximately 10 L/min. In some embodiments when the PFAS analyte solution contains PFOA as analyte, the sheath gas flow setting is approximately 8 L/min.

In some embodiments, the ESI sheath gas flow setting is set on an AGILENT 6490 or 6495 mass spectrometer. In exemplary embodiments, the ESI sheath gas flow setting is set on an AGILENT 6495 mass spectrometer.

In various embodiments of the present invention, concentrations and amounts of PFAS analytes in solutions such as unconcentrated samples are analyzed using ESI conditions that include a capillary voltage setting ("Capillary (V)") of approximately 1500 V to approximately 4500 V. In some embodiments, the capillary voltage setting is approximately 1500 V to approximately 4400 V. In some embodiments, the capillary voltage setting is approximately 1500 V to approximately 4300 V. In some embodiments, the capillary voltage setting is approximately 1500 V to approximately 4200 V. In some embodiments, the capillary voltage setting is approximately 1500 V to approximately 4100 V. In some embodiments, the capillary voltage setting is approximately 1500 V to approximately 4000 V. In some embodiments, the capillary voltage setting is approximately 1500 V to approximately 3900 V. In some embodiments, the capillary voltage setting is approximately 1500 V to approximately 3800 V. In some embodiments, the capillary voltage setting is approximately 1500 V to approximately 3700 V. In some embodiments, the capillary voltage setting is approximately 1500 V to approximately 3600 V. In some embodiments, the capillary voltage setting is approximately 1500 V to approximately 3500 V. In some embodiments, the capillary voltage setting is approximately 1500 V to approximately 3400 V. In some embodiments, the capillary voltage setting is approximately 1500 V to approximately 3300 V. In some embodiments, the capillary voltage setting is approximately 1500 V to approximately 3200 V. In some embodiments, the capillary voltage setting is approximately 1500 V to approximately 3100 V. In some embodiments, the capillary voltage setting is approximately 1500 V to approximately 3000 V. In some embodiments, the capillary voltage setting is approximately 1500 V to approximately 2900 V. In some embodiments, the capillary voltage setting is approximately 1500 V to approximately 2800 V. In some embodiments, the capillary voltage setting is approximately 1500 V to approximately 2700 V. In some embodiments, the capillary voltage setting is approximately 1500 V to approximately 2600 V. In some embodiments, the capillary voltage setting is approximately 1500 V to approximately 2500 V. In some embodiments, the capillary voltage setting is approximately 1500 V to approximately 2400 V. In some embodiments, the capillary voltage setting is approximately 1500 V to approximately 2300 V. In some embodiments, the capillary voltage setting is approximately 1500 V to approximately 2200 V. In some embodiments, the capillary voltage setting is approximately 1500 V to approximately 2100 V. In some embodiments, the capillary voltage setting is approximately 1500 V to approximately 2000 V. In some embodiments, the capillary voltage setting is approximately 1500 V to approximately 1900 V. In some embodiments, the capillary voltage setting is approximately 1500 V to approximately 1800 V. In some embodiments, the capillary voltage setting is approximately 1500 V to approximately 1700 V. In some embodiments, the capillary voltage setting is approximately 1500 V to approximately 1600 V. In some embodiments, the capillary voltage setting is approximately 1500 V.

In various embodiments of the present invention, concentrations and amounts of PFAS analytes in solutions such as unconcentrated samples are analyzed using ESI conditions include a capillary voltage setting of approximately 4500 V. In some embodiments, the capillary voltage setting is approximately 4400 V. In some embodiments, the capillary voltage setting is approximately 4300 V. In some embodiments, the capillary voltage setting is approximately 4200 V. In some embodiments, the capillary voltage setting is approximately 4100 V. In some embodiments, the capillary voltage setting is approximately 4000 V. In some embodiments, the capillary voltage setting is approximately 3900 V. In some embodiments, the capillary voltage setting is approximately 3800 V. In some embodiments, the capillary voltage setting is approximately 3700 V. In some embodiments, the capillary voltage setting is approximately 3600 V. In some embodiments, the capillary voltage setting is approximately 3500 V. In some embodiments, the capillary voltage setting is approximately 3400 V. In some embodiments, the capillary voltage setting is approximately 3300 V. In some embodiments, the capillary voltage setting is approximately 3200 V. In some embodiments; the capillary voltage setting is approximately 3100 V. In some embodiments, the capillary voltage setting is approximately 3000 V. In some embodiments, the capillary voltage setting is approximately 2900 V. In some embodiments, the capillary voltage setting is approximately 2800 V. In some embodiments, the capillary voltage setting is approximately 2700 V. In some embodiments, the capillary voltage setting is approximately 2600 V. In some embodiments, the capillary voltage setting is approximately 2500 V. In some embodiments, the capillary voltage setting is approximately 2400 V. In some embodiments, the capillary voltage setting is approximately 2300 V. In some embodiments, the capillary voltage setting is approximately 2200 V. In some embodiments, the capillary voltage setting is approximately 2100 V. In some embodiments, the capillary voltage setting is approximately 2000 V. In some embodiments, the capillary voltage setting is approximately 1900 V. In some embodiments, the capillary voltage setting is approximately 1800 V. In some embodiments, the capillary voltage setting is approximately 1700 V. In some embodiments, the capillary voltage setting is approximately 1600 V.

In some embodiments when the PFAS analyte solution includes PFBA as analyte, the capillary voltage setting ranges from approximately 1500 V to approximately 2000 V. In some embodiments when the PFAS analyte solution includes PFBA as analyte, the capillary voltage setting is approximately 1500 V.

In some embodiments when the PFAS analyte solution includes PFBS as analyte, the capillary voltage setting ranges from approximately 1500 V to approximately 2500 V. In some embodiments when the PFAS analyte solution includes PFBS as analyte, the capillary voltage setting is approximately 1500 V.

In some embodiments when the PFAS analyte solution includes PFHpA as analyte, the capillary voltage setting ranges from approximately 1500 V to approximately 3000 V. In some embodiments when the PFAS analyte solution includes PFHpA as analyte, the capillary voltage setting is approximately 1500 V.

In some embodiments when the PFAS analyte solution includes PFHxA as analyte, the capillary voltage setting ranges from approximately 1500 V to approximately 3000 V. In some embodiments when the PFAS analyte solution includes PFHxA as analyte, the capillary voltage setting is approximately 1500 V.

In some embodiments when the PFAS analyte solution includes PFHxS as analyte, the capillary voltage setting ranges from approximately 1500 V to approximately 3000 V. In some embodiments when the PFAS analyte solution includes PFHxS as analyte, the capillary voltage setting is approximately 1500 V.

In some embodiments when the PFAS analyte solution includes PFPeS as analyte, the capillary voltage setting ranges from approximately 1500 V to approximately 2500 V. In some embodiments when the PFAS analyte solution includes PFPeS as analyte, the capillary voltage setting is approximately 1500 V.

In some embodiments when the PFAS analyte solution includes PFDA as analyte, the capillary voltage setting ranges from approximately 1500 V to approximately 4500 V. In some embodiments when the PFAS analyte solution includes PFDA as analyte, the capillary voltage setting is approximately 1500 V.

In some embodiments when the PFAS analyte solution includes PFHpS as analyte, the capillary voltage setting ranges from approximately 1500 V to approximately 3000 V. In some embodiments when the PFAS analyte solution includes PFHpS as analyte, the capillary voltage setting is approximately 1500 V.

In some embodiments when the PFAS analyte solution includes PFOS as analyte, the capillary voltage setting ranges from approximately 1500 V to approximately 2500 V. In some embodiments when the PFAS analyte solution includes PFOS as analyte, the capillary voltage setting is approximately 1500 V.

In some embodiments when the PFAS analyte solution includes PFNA as analyte, the capillary voltage setting ranges from approximately 1500 V to approximately 4000 V. In some embodiments when the PFAS analyte solution includes PFNA as analyte, the capillary voltage setting is approximately 1500 V.

In some embodiments when the PFAS analyte solution includes PFNS as analyte, the capillary voltage setting ranges from approximately 1500 V to approximately 4000 V. In some embodiments when the PFAS analyte solution includes PFNS as analyte, the capillary voltage setting is approximately 1500 V.

In some embodiments when the PFAS analyte solution includes PFOA as analyte, the capillary voltage setting ranges from approximately 1500 V to approximately 3000 V. In some embodiments when the PFAS analyte solution includes PFOA as analyte, the capillary voltage setting is approximately 1500 V.

In some embodiments, the ESI capillary voltage setting is set on an AGILENT 6490 or 6495 mass spectrometer. In exemplary embodiments, the ESI capillary voltage setting is set on an AGILENT 6495 mass spectrometer.

In various embodiments, ESI conditions include a gas flow setting ("Gas Flow (1/min)") of approximately 11 L/min to approximately 20 L/min. In some embodiments, the gas flow setting is approximately 11 L/min to approximately 19 L/min. In some embodiments, the gas flow setting is approximately 11 L/min to approximately 18 L/min. In some embodiments, the gas flow setting is approximately 11 L/min to approximately 17 L/min. In some embodiments, the gas flow setting is approximately 11 L/min to approximately 16 L/min. In some embodiments, the gas flow setting is approximately 11 L/min to approximately 15 L/min. In some embodiments, the gas flow setting is approximately 11 L/min to approximately 14 L/min. In some embodiments, the gas flow setting is approximately 11 L/min to approximately 13 L/min. In some embodiments, the gas flow setting is approximately 11 L/min to approximately 12 L/min. In some embodiments, the gas flow setting is approximately 11 L/min.

In various embodiments, ESI conditions include a gas flow setting of approximately 20 L/min. In some embodiments, the gas flow setting is approximately 19 L/min. In some embodiments, the gas flow setting is approximately 18 L/min. In some embodiments, the gas flow setting is approximately 17 L/min. In some embodiments, the gas flow setting is approximately 16 L/min. In some embodiments, the gas flow setting is approximately 15 L/min. In some embodiments, the gas flow setting is approximately 14 L/min. In some embodiments, the gas flow setting is approximately 13 L/min. In some embodiments, the gas flow setting is approximately 12 L/min.

In some embodiments when the PFAS analyte solution includes PFBA as analyte, the gas flow setting ranges from approximately 11 L/min to approximately 20 L/min. In some embodiments when the PFAS analyte solution includes PFBA as analyte, the gas flow setting is approximately 11 L/min.

In some embodiments when the PFAS analyte solution contains PFBS as analyte, the gas flow setting ranges from approximately 11 L/min to approximately 20 L/min. In some embodiments when the PFAS analyte solution includes PFBS as analyte, the gas flow setting is approximately 11 L/min.

In some embodiments when the PFAS analyte solution contains PFHpA as analyte, the gas flow setting ranges from approximately 11 L/min to approximately 20 L/min. In some embodiments when the PFAS analyte solution includes PFHpA as analyte, the gas flow setting is approximately 11 L/min.

In some embodiments when the PFAS analyte solution contains PFHxA as analyte, the gas flow setting ranges from approximately 11 L/min to approximately 20 L/min. In some embodiments when the PFAS analyte solution includes PFHxA as analyte, the gas flow setting is approximately 11 L/min.

In some embodiments when the PFAS analyte solution contains PFHxS as analyte, the gas flow setting ranges from approximately 11 L/min to approximately 20 L/min. In some embodiments when the PFAS analyte solution includes PFHxS as analyte, the gas flow setting is approximately 11 L/min.

In some embodiments when the PFAS analyte solution contains PFPeS as analyte, the gas flow setting ranges from approximately 11 L/min to approximately 20 L/min. In some embodiments when the PFAS analyte solution includes PFPeS as analyte, the gas flow setting is approximately 11 L/min.

In some embodiments when the PFAS analyte solution contains PFDA as analyte, the gas flow setting ranges from approximately 11 L/min to approximately 20 L/min. In some embodiments when the PFAS analyte solution includes PFDA as analyte, the gas flow setting is approximately 11 L/min.

In some embodiments when the PFAS analyte solution contains PFHpS as analyte, the gas flow setting ranges from approximately 11 L/min to approximately 20 L/min. In some embodiments when the PFAS analyte solution includes PFHpS as analyte, the gas flow setting is approximately 11 L/min.

In some embodiments when the PFAS analyte solution contains PFOS as analyte, the gas flow setting ranges from approximately 11 L/min to approximately 12 L/min. In some embodiments when the PFAS analyte solution includes PFOS as analyte, the gas flow setting is approximately 11 L/min.

In some embodiments when the PFAS analyte solution contains PFNA as analyte, the gas flow setting ranges from approximately 11 L/min to approximately 20 L/min. In some embodiments when the PFAS analyte solution includes PFNA as analyte, the gas flow setting is approximately 11 L/min.

In some embodiments when the PFAS analyte solution contains PFNS as analyte, the gas flow setting ranges from approximately 11 L/min to approximately 20 L/min. In some embodiments when the PFAS analyte solution includes PFNS as analyte, the gas flow setting is approximately 11 L/min.

In some embodiments when the PFAS analyte solution contains PFOA as analyte, the gas flow setting ranges from approximately 11 L/min to approximately 20 L/min. In some embodiments when the PFAS analyte solution includes PFOA as analyte, the gas flow setting is approximately 11 L/min.

In some embodiments, the ESI gas flow setting is set on an AGILENT 6490 or 6495 mass spectrometer. In exemplary embodiments, the ESI gas flow setting is set on an AGILENT 6495 mass spectrometer.

An example of minimum detection levels (MDL), minimum reporting levels (RL or MRL), and reporting ranges for the ESI settings shown above is shown in Table 3.

TABLE 3

Minimum Detection Levels (MDL), Minimum Reporting Levels (RL or MRL), and Reporting Ranges for an Exemplary Embodiment of the Present Invention.

| Acronym | MDL [µg/L] | RL (MRL) [µg/L] | Reporting Range [µg/L] |
| --- | --- | --- | --- |
| PFBA | 0.0025 | 0.010 | 0.010-0.25 |
| PFBS | 0.0041 | 0.010 | 0.010-0.25 |
| PFDA | 0.0044 | 0.010 | 0.010-0.25 |
| PFHpA | 0.0055 | 0.010 | 0.010-0.25 |
| PFHpS | 0.0087 | 0.010 | 0.010-0.25 |
| PFHxA | 0.0017 | 0.010 | 0.010-0.25 |
| PFHxS | 0.0057 | 0.010 | 0.010-0.25 |
| PFNA | 0.0052 | 0.010 | 0.010-0.25 |
| PFPeS | 0.0045 | 0.010 | 0.010-0.25 |
| PFOA | 0.00077 | 0.0020 | 0.0020-0.25 |
| PFOS | 0.00095 | 0.0020 | 0.0020-0.25 |

MDLs (Method Detection Limits) are statistical values used to determine RLs/MRLs as described infra.

RLs/MRLs (Reporting Limits or Minimum Reporting Levels) are practical and routinely achievable values of analyte concentration given ESI parameters such as described supra. The determination of RLs/MRLs is described infra.

Figure 2:
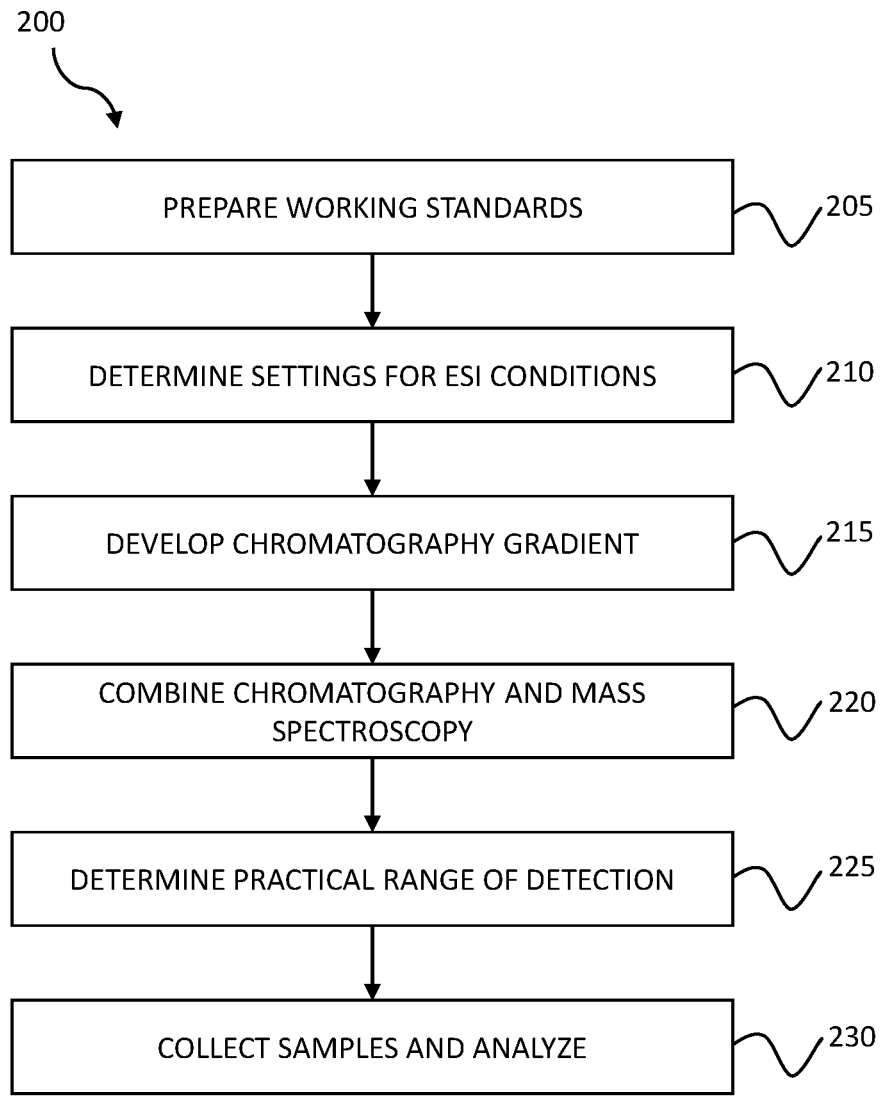
FIG. 2 illustrates processes for validating a method to determine concentrations and amounts of PFAS analytes in solutions and/or unconcentrated samples, in accordance with an exemplary embodiment of the present invention.

FIG. 2 illustrates processes, generally designated 200, for validating a method to determine concentrations and amounts of PFAS analytes in unconcentrated samples and consequently determining concentrations and amounts of PFAS analytes in unconcentrated samples, in accordance with an exemplary embodiment of the present invention.

In step 205, working standards of PFAS analytes are prepared. Working standards include standards to calibrate and verify the calibration of the LC/MS/MS system both initially and ongoing (described in more detail infra) as well as quality control standards analyzed in an analytical run such as laboratory fortified blanks, laboratory fortified matrix standards, laboratory fortified matrix duplicates, etc. Laboratory fortified blanks are an aliquot of preserved reagent water to which known quantities of the method analytes are added in the laboratory. Laboratory fortified blanks are analyzed like samples. The laboratory fortified blanks are used to determine whether a method can make accurate and precise measurements. Laboratory fortified matrix standards are aliquots of environmental samples to which known quantities of the method analytes are added in the laboratory. Laboratory fortified matrix standards are analyzed like samples. The laboratory fortified matrix standards are used to determine whether a sample matrix contributes bias to the analytical results. The background concentrations of the analytes in the sample matrix are determined in a separate aliquot and the measured values in the laboratory fortified matrix standards are corrected for background concentrations. Laboratory fortified matrix duplicates are a second aliquot of the environmental sample used to prepare the laboratory fortified matrix standards. They are fortified, processed, and analyzed identically to the laboratory fortified matrix standards. Laboratory fortified matrix duplicates are used instead of a laboratory duplicate to assess method precision when the occurrence of target analytes is low.

In some embodiments, a quality control sample is a solution of method analytes obtained from a source external to the laboratory and different from the source of calibration standards. The quality control sample is used to verify the accuracy of the calibration standards.

Preserved reagent water is deionized water (resistance of 18.2 megaohms or greater) wherein a preservative has been added. In one embodiment, preserved reagent includes the addition of approximately 200 mg of ammonium chloride per liter of deionized water.

As used herein, "fortified" indicates that the sample, standard, blank, etc. has the one or more target PFAS analytes added to the solution. In other words, the sample, standard, blank, etc. that is "fortified" has had the target analyte added in a specified amount to the fortified sample, standard, blank, etc.

Because the inventive method and system concerns PFAS detection at ppt levels, Teflon products are fastidiously excluded. If PFAS contamination is unavoidable from the LC/MS/MS system, the detection of such contamination is not integrated or included in the determination of concentration and/or amount of the PFAS in question. The use of blanks allows detection of such contamination and correction is taken based on such detection. Blank subtraction is not a valid or acceptable correction for contamination.

A continuing calibration verification standard (CCV) is a calibration standard containing a specified concentration of method analytes, which is analyzed at specified periods to verify the accuracy of the existing calibration for said analytes. For some embodiments of the present invention, there is no substantially significant difference between a laboratory fortified blank and a continuing calibration verification standard.

A laboratory fortified matrix standard is an aliquot of an environmental sample to which known quantities of method analytes are added in the laboratory. The laboratory fortified matrix standard is analyzed like a sample, and its purpose is to determine whether the sample matrix contributes bias to the analytical results. The background concentrations of the analytes in the sample matrix should preferably be determined in a separate aliquot and the measured values in the laboratory fortified matrix standard corrected for background concentrations. In various embodiments, a laboratory fortified matrix duplicate standard is a second aliquot of an environmental sample used to prepare the laboratory fortified matrix standard. The laboratory fortified matrix duplicate standard is fortified, processed, and analyzed in the same way as the laboratory fortified matrix standard. The laboratory fortified matrix standard duplicate is used instead of a laboratory duplicate to assess method precision when the occurrence of target analytes is low.

Method blanks are aliquots of preserved reagent water that are treated exactly as a sample including exposure to all glassware, equipment, solvents, reagents, etc. In various embodiments, the method blanks are used to determine if method analytes or other interferences are present in the laboratory environment, the reagents, or the apparatus.

An internal standard is a pure compound added equally and in a known amount to all standard solutions and samples. They are used to measure the relative response of the method analyte. In some embodiments, the internal standard includes isotopically labeled analogues (e.g., 13C) of method analyte.

In some embodiments, an analysis batch is analyzed on the LC/MS/MS system. An analysis batch is a set of up to 20 field samples (not including quality control samples such as method blanks, continuing calibration verification standards, laboratory fortified matrix standards and laboratory fortified matrix duplicate standards) that are analyzed on the same instrument during a 24-hour period that begins and ends with the analysis of the appropriate continuing calibration verification standard. In some embodiments, an additional continuing calibration verification standard is analyzed after analysis of 10 field samples.

Standards for initial calibration, ongoing calibration verification, and quality control samples, etc. are prepared by adding appropriate volumes of primary dilution standard solutions to preserved reagent water or sample. Primary dilution standard (PDS) solutions are solutions of one or more method analytes prepared in the laboratory from stock standard solutions and diluted as needed to prepare calibration solutions and other required analyte solutions. Stock standard solutions are concentrated solutions containing one or more method analytes prepared in the laboratory using assayed reference materials or purchased as certified from a reputable commercial source. For example, standards or other solutions of desired concentrations may be prepared from primary dilution standard solutions or a stock standard solutions if the desired concentrations are more dilute than the primary dilution standard solutions or a stock standard solutions. Analogously, serial dilution of, e.g., calibration standards of a given concentration, provide calibration standards lower and lower in concentration than the given concentration with every dilution.

Table 4 shows an example for the preparation of stock standard and primary dilution standards.

TABLE 4

Stock Standards (SS) and Primary Dilution Standards (PDS) Example Preparation.

| | Stock Standard Custom Mix-(SS) | | | Primary dilution Standards (PDS) | | | |
|---|---|---|---|---|---|---|---|
| Analyte | Weight (g)[3] | Volume (mL)[4] | Conc.[5] (mg/mL) | Volume of SS used ($\propto$L) | Conc. ($\propto$g/mL) | Final Volume (mL)[6] | Standard ID |
| PFOS*[1] | 0.0538 | 50.00 | 1.00 | 2.50 | 0.10 | 25.00 | PDS 1 |
| PFHxS*[1] | 0.0548 | | 1.00 | 2.50 | | | |
| PFBA | Purchased as | | 0.0500 | 50.00 | | | |
| PFBS* | solution of indicated | | 0.0442 | 57.00 | | | |
| PFDA | concentration. | | 0.0500 | 50.00 | | | |
| PFHpA | | | 0.0500 | 50.00 | | | |
| PFHpS** | | | 0.0476 | 52.0 | | | |
| PFHxA | | | 0.0500 | 50.00 | | | |
| PFNA | | | 0.0500 | 50.00 | | | |
| PFPeS** | | | 0.0469 | 53.00 | | | |
| PFOA | | | 0.0500 | 50.00 | | | |
| PFOS*[1] | 0.0323 | 30.00 | 1.00 | 2.50 | 0.10 | 25.00 | PDS 2 |
| PFHxS*[1] | 0.0329 | | 1.00 | | | | |
| PFBA | 0.0300 | | 1.00 | | | | |
| PFBS | | | 1.00 | | | | |
| PFDA | | | 1.00 | | | | |
| PFHxA | | | 1.00 | | | | |
| PFNA | | | 1.00 | | | | |
| PFHxA | | | 1.00 | | | | |
| PFOA***[2] | Analytes purchased | | 0.0414 | 60.4 | | | |
| PFHpS** | as solution of | | 0.0476 | 52.00 | | | |
| PFPeS** | indicated concentration. | | 0.0469 | 53.00 | | | |
| 13C-PFHxA | Analytes purchased as solution of indicated concentration. | | 0.05000 | 15.00 | 0.0075 | 100.00 | IS |
| 13C-PFDA | | | | | | | |
| 13C-PFOA | | | | | | | |
| 13C-PFOS** | | | 0.0478 | 15.70 | | | |

*Potassium salt
**Sodium salt
***Ammonium salt
[1]Technical grade quantitative standards containing branch and linear isomers
[2]Technical grade qualitative standard containing branch and linear isomers
[3]Analyte compound purchased neat from vendor.
[4]Weighed analyte dissolved with indicated volume of methanol.
[5]After dilution with methanol.
[6]After dilution with methanol.

Table 5 shows an example for the preparation of working standards.

TABLE 5

Example Preparation of Working Standards (WS).

| WS Name | Volume of PDS/ICS Used (∝L) | WS Final Volume (mL) | Solvent Used | WS Final Concentration (∝g/L) |
|---|---|---|---|---|
| ICS 6/CCV HL | 250/PDS1 | 100.00 | Preserved reagent water | 0.25 |
| ICS 5/CCVML | 100/PDS1 | 100.00 | | 0.10 |
| ICS 1/CCV LLa | 100/ICS 5 | 5.00 | | 0.0020 |
| ICS 2/CCV LLb | 500/ICS 5 | 5.00 | | 0.010 |
| ICS 3 | 1250/ICS 5 | 5.00 | | 0.025 |
| ICS 4 | 2500/ICS 5 | 5.00 | | 0.050 |
| MDL a | 50/ICS 5 | 5.00 | | 0.0010 |
| MDL b | 250/ICS 5 | 5.00 | | 0.0050 |
| LFB ML (for DOC) | 2500/ICS 5 | 5.00 | | 0.050 |
| QCS | 50.0/PDS2 | 100.00 | | 0.050 |
| LFM/LFMD | 50.0/PDS1 | 100.00 | Sample | 0.050 |

100.0 ∝L of IS is added to 5.00 mL of each WS resulting in a concentration of 0.15 ∝g/L.
ICS 1 is only used for PFOS and PFOA.
The RL for PFOS and PFOA is 0.0020 ∝g/L, the RL for all other compounds is 0.010 ∝g/L In step 210, acceptable settings are determined for ESI mass spectrometer conditions of individual PFAS analytes and mixtures thereof as described supra. An example of ESI mass spectrometer conditions is shown in Table 2 (supra).

In step 215, a chromatography gradient is developed that allows the analysis of PFAS mixtures analyzed in the present invention. An example of a chromatography gradient suitable for separation and analysis of PFAS mixtures is shown in Table 6.

TABLE 6

Example of an LC Gradient for PFAS Analysis of PFAS.
LC Gradient Program for PFAS Analysis

| Time (min) | % 5 mM Ammonium Acetate | % Methanol |
|---|---|---|
| 0 | 85 | 15 |
| 1 | 85 | 15 |
| 3 | 5 | 95 |
| 5 | 5 | 95 |
| 5.1 | 85 | 15 |
| 6.6 | 85 | 15 |

In step 220 the chromatographic gradient developed in step 215 is combined with the mass spectroscopy settings determined in step 210. Table 7 shows an example of triple quadrapole MS/MS method conditions for PFAS analysis after combination with the Table 6 LC gradient. The chromatographic gradient and mass spectroscopy conditions must be optimized to allow an appropriate number of scans across the peak. To produce good, reproducible peak shape and recoveries, a minimum of 10 scans across the peak is required.

TABLE 7

Example of LC/MS/MS Method Conditions for PFAS Analysis.
Triple Quadrupole MS/MS Method Conditions

| Analyte | Scan Type | Retention Time (min) | Precursor Ion (m/z) | Product Ion (m/z)$^a$ | MS1 MS2 | Frag Voltage | Collision Energy (ev)$^b$ | Cell Acceleration (V) | Int Std Used for Quantitation |
|---|---|---|---|---|---|---|---|---|---|
| PFBA | Primary | 3.97 | 212.99 | 168.9 | Unit | 380 | 5 | 4 | PFHxA 13C |
| PFBS | Primary | 5.529 | 298.99 | 98.8 | Unit | 380 | 37 | 1 | PFOS 13C |
| PFBS | Qualifier | 5.529 | 298.99 | 80 | Unit | 380 | 41 | 1 | |
| PFDA | Primary | 6.068 | 512.99 | 468.9 | Unit | 380 | 9 | 3 | PFDA 13C |
| PFDA | Qualifier | 6.068 | 512.99 | 218.9 | Unit | 380 | 17 | 3 | |
| PFDA 13C | Internal Standard | 6.068 | 514.99 | 470.4 | Unit | 380 | 9 | 3 | NA |
| PFHpA | Primary | 5.815 | 362.99 | 318.8 | Unit | 380 | 5 | 1 | PFHxA 13C |
| PFHpA | Qualifier | 5.815 | 362.99 | 168.9 | Unit | 380 | 17 | 1 | |
| PFHpS | Primary | 5.905 | 448.99 | 98.7 | Unit | 380 | 45 | 1 | PFOS 13C |
| PFHpS | Qualifier | 5.905 | 448.99 | 80.1 | Unit | 380 | 45 | 1 | |
| PFHxA | Primary | 5.686 | 312.99 | 268.9 | Unit | 380 | 5 | 2 | PFHxA 13C |
| PFHxA | Qualifier | 5.686 | 312.99 | 119 | Unit | 380 | 21 | 2 | |
| PFHxA 13C | Internal Standard | 5.686 | 314.99 | 270.1 | Unit | 380 | 5 | 2 | NA |
| PFHxS | Primary | 5.805 | 398.99 | 98.9 | Unit | 380 | 41 | 2 | PFOS 13C |
| PFHxS | Qualifier | 5.805 | 398.99 | 79.9 | Unit | 380 | 55 | 2 | |
| PFNA | Primary | 5.997 | 462.99 | 419.1 | Unit | 380 | 5 | 4 | PFHxA 13C |
| PFNA | Qualifier | 5.997 | 462.99 | 218.9 | Unit | 380 | 17 | 4 | |
| PFOA | Primary | 5.915 | 412.99 | 368.9 | Unit | 380 | 4 | 4 | PFOA 13C |
| PFOA | Qualifier | 5.915 | 412.99 | 168.8 | Unit | 380 | 17 | 4 | |
| PFOA 13C | Internal Standard | 5.848 | 414.99 | 370 | Unit | 380 | 5 | 4 | NA |
| PFOS | Primary | 5.987 | 498.99 | 98.8 | Unit | 380 | 45 | 2 | PFOS 13C |
| PFOS | Qualifier | 5.987 | 498.99 | 79.9 | Unit | 380 | 55 | 2 | |
| PFOS 13C | Internal Standard | 5.987 | 502.99 | 79.8 | Unit | 380 | 52 | 2 | NA |
| PFPeS | Primary | 5.694 | 348.99 | 98.8 | Unit | 380 | 41 | 2 | PFHxA 13C |
| PFPeS | Qualifier | 5.694 | 348.99 | 79.9 | Unit | 380 | 41 | 2 | |

For Table 7, the precursor ion is the deprotonated molecule ([M-H]—) of the target analyte. In MS/MS, the precursor ion is mass selected and fragmented by collisionally activated dissociation to produce distinctive product ions of smaller m/z. The product ion is one of the fragment ions produced in MS/MS by the collisionally activated dissociation of the precursor ion.

In the examples shown in Tables 6 and 7 the following instrumentation is used:

i) AGILENT LC/MS/MS System (Column: Analytical column ZORBAX ECLIPSE PLUS C18, 2.1×50 mm, 1.8 um);
ii) AGILENT 1290 INFINITY Autosampler;
iii) AGILENT 1290 Binary Pump;
iv) AGILENT 1290 TCC Column Compartment; and
v) AGILENT 6495 Mass Spectrometer.

In the examples shown in Tables 6 and 7 the data software used is AGILENT MASS HUNTER.

In step 225, a practical range of detection is determined using calibration standards prepared as described supra and method validation samples. In these steps, quality control (QC) includes a demonstration of capability (DOC) requirement, a determination of the method detection limit (MDL), and confirmation of the minimum reporting limit (MRL).

In various embodiments, an initial demonstration of capability (IDC) is performed prior to analyzing any field samples and any time major method modifications are made. The following steps are exemplary:

i) Generate an acceptable instrument calibration and demonstrate a low system background by analyzing an acceptable method blank. The mass spectrometer is calibrated according to the manufacturer's recommendations. Prior to the analysis of samples, the instrument's performance is optimized, and an instrument calibration curve is generated. The instrument is calibrated using standards at several concentrations. They are analyzed with every analytical run. A calibration curve is generated for each analyte by plotting the responses against known concentrations. In some embodiments, linear and/or quadratic regression models are used. Both weighted and unweighted models are used. In various embodiments, a calibration curve regression model and a range of calibration levels is used for all routine sample analysis. The initial calibration is verified by analyzing various concentrations of CCV ((low level) LL, (medium level) ML, (high level) HL) prior to sample analysis and after every 10 samples (see Table 5 supra).

ii) Analyze a method blank to demonstrate low background contamination.

iii) Demonstrate method precision and accuracy by analyzing 4 replicates of a laboratory fortified method blank.

iv) Establish the method detection limit (MDL) by analyzing seven replicates of a laboratory fortified blank fortified at less than the concentration of the reporting limits (RL) over a period of three days. The determination of the MDL is described in more detail infra.

Table 8 illustrates an example of a laboratory analytical run sequence for this method, with QC parameters frequency, concentrations and acceptance criteria.

TABLE 8

Method Analysis Sequence with QC Frequency and Acceptance Criteria.

| Anal # | Sample Name | QCs, ICSs, CCVs Acceptance Criteria | QC and Instrument Calibration Frequency |
|---|---|---|---|
| 1 | ICS 1 | 1. Instrument Calibration is updated and recalculated against the newly generated calibration curve. | Analyzed with every analytical run. |
| 2 | ICS 2 | | |
| 3 | ICS 3 | | |
| 4 | ICS 4 | | |
| 5 | ICS 5 | 2. Each analyte in each calibration point, except for the concentrations ≤RL, must calculate to be ±30% of the true value. | |
| 6 | ICS 6 | | |
| | | 3. Each analyte in calibration points at concentrations ≤RL must calculate to be ±50% of the true value. | |
| | | 4. ICS 1 is only used for PFOS and PFOA. | |
| 7 | QCS | 1. Recovery for target analytes must be ±30% of the true value | Analyzed after instrument calibration |
| 8 | MB | 1. Must be free from contamination that could prevent the determination of any target analyte. Concentration of target analytes must be ≤1/3 RL. | Analyzed with each batch of up to 20 samples processed as a group within a work shift. |
| 9 | CCV LLa | 1. Recovery for PFOA and PFOS must be ± 50% of the true value | Analyzed at the beginning of an analytical batch of 20 samples processed as a group within a work shift. |
| 10 | CCV LLb | 1. Recovery for target analytes must be ±50% of the true value. | |
| 11 | Sample 1* | | |
| 12 | LFM | 1. LFM/D: Recovery for target analytes should be ±40% of the true value for all analytes except for PFOA and PFOS should be ± 30% of the true value f; precision as RPD should | Analyzed with each batch of up to 20 samples processed as a group within a work shift. |
| 13 | LFMD | | |
| 14 | Sample 2* | | |
| 15 | Sample 3* | | |
| 16 | Sample 4* | | |
| 17 | Sample 5* | | |

TABLE 8-continued

Method Analysis Sequence with QC Frequency and Acceptance Criteria.

| Anal # | Sample Name | QCs, ICSs, CCVs Acceptance Criteria | QC and Instrument Calibration Frequency |
|---|---|---|---|
| 18 | Sample 6* | be ≤30%. | |
| 19 | Sample 7* | | |
| 20 | Sample 8* | | |
| 21 | Sample 9* | | |
| 22 | Sample 10* | | |
| 23 | CCV ML | 1. Recovery for target analytes must be ±30% of the true value. | Analyzed with each analytical batch of up to 20 samples after the first 10 samples. |
| 24 | Sample 11* | | |
| 25 | Sample 1* | | |
| 26 | Sample 13* | | |
| 27 | Sample 14* | | |
| 28 | Sample 15* | | |
| 29 | Sample 16* | | |
| 30 | Sample 17* | | |
| 31 | Sample 18* | | |
| 32 | Sample 19* | | |
| 33 | Sample 20* | | |
| 34 | CCV HL | 1. Recovery for target analytes must be ±30% of the true value. | Analyzed with each analytical batch of up to 20 samples after the second 10 samples. |

Internal Standard Response Relative Percent Deviation (ISRPD) must not exceed ±50% for each analyte except PFDA.
ISRPD for PFDA must not exceed ±60%
*If sample contains a method analyte(s) at or above the MRL, analyze an associated FB.
If a method analyte(s) found in the field sample is present in the associated FB at a concentration greater than 1/3MRL, then the sample results are invalid.

An example of a demonstration of capability (DOC) study including the demonstration of laboratory precision and accuracy are presented in Table 9 using 75 μL injection volumes:

TABLE 9

Example of a DOC Study for PFAS.

| | | Data File | | | | | | | | |
|---|---|---|---|---|---|---|---|---|---|---|
| | | 17 | 18 | 19 | 20 | | Accuracy | Method's | | Precision | Method's |
| | Amount | Amount Recovered | | | | | as Mean | Accuracy | Standard | as | Precision |
| Analyte Name | Added [μg/L] | DEMO [μg/L] | DEMO [μg/L] | DEMO [μg/L] | DEMO [μg/L] | Mean [μg/L] | Recovery [%] | Limits [%] | Deviation [μg/L] | RSD * [%] | Limits [%] |
| PFBA | 0.050 | 0.0524 | 0.0482 | 0.0478 | 0.0477 | 0.049 | 98.0 | 70.0-130.0 | 0.0023 | 4.6 | <20.0 |
| PFBS | 0.050 | 0.0413 | 0.0452 | 0.0430 | 0.0434 | 0.043 | 86.5 | 70.0-130.0 | 0.0016 | 3.6 | <20.0 |
| PFHxA | 0.050 | 0.0483 | 0.0495 | 0.0430 | 0.0454 | 0.047 | 93.1 | 70.0-130.0 | 0.0029 | 6.3 | <20.0 |
| PFPeS | 0.050 | 0.0522 | 0.0472 | 0.0476 | 0.0506 | 0.049 | 98.8 | 70.0-130.0 | 0.0024 | 4.9 | <20.0 |
| PFHpA | 0.050 | 0.0542 | 0.0518 | 0.0468 | 0.0504 | 0.051 | 101.6 | 70.0-130.0 | 0.0031 | 6.1 | <20.0 |
| PFHxS | 0.050 | 0.0484 | 0.0504 | 0.0508 | 0.0482 | 0.049 | 98.9 | 70.0-130.0 | 0.0013 | 2.7 | <20.0 |
| PFHpS | 0.050 | 0.0522 | 0.0610 | 0.0584 | 0.0565 | 0.057 | 114.0 | 70.0-130.0 | 0.0037 | 6.5 | <20.0 |
| PFOA | 0.050 | 0.0487 | 0.0542 | 0.0489 | 0.0502 | 0.050 | 101.0 | 70.0-130.0 | 0.0026 | 5.1 | <20.0 |
| PFOS | 0.050 | 0.0491 | 0.0517 | 0.0546 | 0.0538 | 0.052 | 104.6 | 70.0-130.0 | 0.0025 | 4.7 | <20.0 |
| PFNA | 0.050 | 0.0616 | 0.0516 | 0.0517 | 0.0547 | 0.055 | 109.8 | 70.0-130.0 | 0.0047 | 8.5 | <20.0 |
| PFDA | 0.050 | 0.0490 | 0.0539 | 0.0488 | 0.0535 | 0.051 | 102.6 | 70.0-130.0 | 0.0028 | 5.4 | <20.0 |

Determination of MDL

MDL (Method Detection Limits) are the minimum concentration of a substance that can be reported with 99% confidence that the measured concentration is distinguishable from Method Blank results. An example of a procedure for determining MDL is as follows:

First, an estimate is made of an initial MDL using one or more of: i) a mean determined concentration plus three times the standard deviation of a set of MB; ii) a concentration value that corresponds to an instrument signal/noise in the range of 3 to 5; iii) a concentration equivalent of three times the standard deviation of replicate instrumental measurements of spiked blanks; iv) a region of the calibration where there is a significant change in sensitivity, such as a break in the slope of the calibration; v) an instrumental limitation; and vi) a previously determined MDL.

Second, an initial MDL determination is made by selecting a spiking level, typically 2-10 times the estimated method detection limit from above, but less than the value of the laboratory established RL and less than or equal to a regulatory authority reported required detection limit (RDL), if one exists. Once the spiking level is determined, a minimum of seven laboratory standards in reagent water (containing all method preservatives, if applicable) are made at the selected spiking level concentration and they are processed through all steps of the method. Generally, the standards used for the MDL are prepared in at least three batches on three separate calendar dates and analyzed on three separate calendar dates. Preparation and analysis may be performed on the same day. In general, statistical outlier removal procedures are not used to remove data for the initial MDL determination since the total number of observations is small and the purpose of the MDL procedure is to capture routine method variability. However, documented instances of gross failures (e.g., instrument malfunctions, mislabeled samples, cracked vials) may be excluded from the calculations, provided that at least seven spiked samples and seven method blanks are available. After the method is run, the spiking level is evaluated. If any result for any individual analyte from the spiked samples does not meet a qualitative method identification criterion or does not provide a numerical result greater than zero, then the method is repeated with spiked samples at a higher concentration.

The method MDL is the greater of either an MDL based on spiked samples (MDLs) or an MDL based on method blanks (MDLb).

The MDL is calculated as shown below:

First, a mean of the measured concentration values X is calculated as shown below:

$$X = \sum \frac{Xi}{n}$$

Where:
i=from 1 to n;
n=the number of data points; and
Xi=the measured concentration value of an individual laboratory standard.

Second, a mean percent recovery (R) is calculated as shown below:

$$R = \frac{X}{T} \times 100\%$$

Where:
X=mean of the measured concentration values; and
T=true concentration used.

Third, a standard deviation (Ss) is calculated as shown below:

$$Ss = \sqrt{\frac{\sum (Xi - X)^2}{n-1}}$$

Where:
i=from 1 to n
n=the number of data points;
Xi=the measured concentration value of an individual laboratory standard; and
X=mean of the measured concentration values.

The MDLs is then calculated as shown below:

MDLs=$t_{(n-1, 1-\alpha=0.99)}$*Ss

Where:
$t_{(n-1, 1-\alpha=0.99)}$=the Student's t-value appropriate for a single-tailed 99$^{th}$ percentile t statistic and a standard deviation estimate with n-1 degrees of freedom (see Table 10 below); and Ss=standard deviation of the replicate spiked sample analyses.

For the MLDb, one of the following criterion is applied:

i) If none of the method blanks give numerical results for an individual analyte, the MDLb does not apply and the MDLs is used. A numerical result includes both positive and negative results, including results below a current MDL, but not results of "ND" (not detected) commonly observed when a peak is not present in chromatographic analysis;

ii) If some (but not all) of the method blanks for an individual analyte give numerical results, set the MDLb equal to the highest method blank result; or iii) If all of the method blanks for an individual analyte give numerical results, then the MDLb is calculated as shown below:

First, a mean of the measured concentration values X is calculated as shown below:

$$X = \sum \frac{Xi}{n}$$

Where:
i=from 1 to n;
n=the number of data points; and
Xi=the measured concentration value of an individual MB.

Second, a standard deviation (Sb) is calculated as shown below:

$$Sb = \sqrt{\frac{\sum (Xi - X)^2}{n-1}}$$

Where:
i=from 1 to n
n=the number of data points;
Xi=the measured concentration value of an individual MB; and
X=mean of the measured MB concentration values.

Third, the MDLb is then calculated as shown below:

MDLb=X+$t_{(n-1, 1-\alpha=0.99)}$*Sb

Where:
X=mean of the MB results (zero is used in place of the mean if the mean is negative);
$t_{(n-1, 1-\alpha=0.99)}$=the Student's t-value appropriate for a single-tailed 99$^{th}$ percentile t statistic and a standard deviation estimate with n-1 degrees of freedom (see Table 8 below); and
Sb=standard deviation of the MB analyses.

TABLE 10

Student's Single-Tailed 99th Percentile t Statistic Values.

| Replicate Number n | Degrees of Freedom n − 1 | Student's t-Value $t_{(n-1, 0.99)}$ | Replicates Number n | Degrees of Freedom n − 1 | Student's t-Value $t_{(n-1, 0.99)}$ | Replicates Number n | Degrees of Freedom n − 1 | Student's t-Value $t_{(n-1, 0.99)}$ |
|---|---|---|---|---|---|---|---|---|
| 7 | 6 | 3.143 | 41 | 40 | 2.423 | 75 | 74 | 2.378 |
| 8 | 7 | 2.998 | 42 | 41 | 2.421 | 76 | 75 | 2.377 |
| 9 | 8 | 2.896 | 43 | 42 | 2.418 | 77 | 76 | 2.376 |
| 10 | 9 | 2.821 | 44 | 43 | 2.416 | 78 | 77 | 2.376 |
| 11 | 10 | 2.764 | 45 | 44 | 2.414 | 79 | 78 | 2.375 |
| 12 | 11 | 2.718 | 46 | 45 | 2.412 | 80 | 79 | 2.374 |
| 13 | 12 | 2.681 | 47 | 46 | 2.410 | 81 | 80 | 2.374 |
| 14 | 13 | 2.650 | 48 | 47 | 2.408 | 82 | 81 | 2.373 |
| 15 | 14 | 2.624 | 49 | 48 | 2.407 | 83 | 82 | 2.373 |
| 16 | 15 | 2.602 | 50 | 49 | 2.405 | 84 | 83 | 2.372 |
| 17 | 16 | 2.583 | 51 | 50 | 2.403 | 85 | 84 | 2.372 |
| 18 | 17 | 2.567 | 52 | 51 | 2.402 | 86 | 85 | 2.371 |
| 19 | 18 | 2.552 | 53 | 52 | 2.400 | 87 | 86 | 2.370 |
| 20 | 19 | 2.539 | 54 | 53 | 2.399 | 88 | 87 | 2.370 |
| 21 | 20 | 2.528 | 55 | 54 | 2.397 | 89 | 88 | 2.369 |
| 22 | 21 | 2.518 | 56 | 55 | 2.396 | 90 | 89 | 2.369 |
| 23 | 22 | 2.508 | 57 | 56 | 2.395 | 91 | 90 | 2.368 |
| 24 | 23 | 2.500 | 58 | 57 | 2.394 | 92 | 91 | 2.368 |
| 25 | 24 | 2.492 | 59 | 58 | 2.392 | 93 | 92 | 2.368 |
| 26 | 25 | 2.485 | 60 | 59 | 2.391 | 94 | 93 | 2.367 |
| 27 | 26 | 2.479 | 61 | 60 | 2.390 | 95 | 94 | 2.367 |
| 28 | 27 | 2.473 | 62 | 61 | 2.389 | 96 | 95 | 2.366 |
| 29 | 28 | 2.467 | 63 | 62 | 2.388 | 97 | 96 | 2.366 |
| 30 | 29 | 2.462 | 64 | 63 | 2.387 | 98 | 97 | 2.365 |
| 31 | 30 | 2.457 | 65 | 64 | 2.386 | 99 | 98 | 2.365 |
| 32 | 31 | 2.453 | 66 | 65 | 2.385 | 100 | 99 | 2.365 |
| 33 | 32 | 2.449 | 67 | 66 | 2.384 | 101 | 100 | 2.364 |
| 34 | 33 | 2.445 | 68 | 67 | 2.383 | ∞ | ∞ | 2.326 |
| 35 | 34 | 2.441 | 69 | 68 | 2.382 | | | |
| 36 | 35 | 2.438 | 70 | 69 | 2.382 | | | |
| 37 | 36 | 2.434 | 71 | 70 | 2.381 | | | |
| 38 | 37 | 2.431 | 72 | 71 | 2.380 | | | |
| 39 | 38 | 2.429 | 73 | 72 | 2.379 | | | |
| 40 | 39 | 2.426 | 74 | 73 | 2.379 | | | |

In general, an MDL verification is performed each time an MDL study is performed and on an annual basis. In one scenario, if an MDL value is greater than or equal to the concentration used for the MDL study, the concentration used for MDL study will be the MDL verification concentration. In another scenario, if an MDL value is less than the concentration used for MDL study, a laboratory standard is prepared and analyzed in reagent water (with preservatives if applicable), wherein the, laboratory standard prepared has an analyte concentration:

i) greater than or equal to the MDL value;

ii) no more than 2-3 times the MDL value;

iii) less than the concentration used for the MDL study and the RL; and iv) less than or equal to the RDL if applicable.

Determination of RL/MRL

The RL (or MRL) is established for each method/analyte using its calculated MDL value. The RL/MRL is set at a value of 1 to 5 times the MDL value and then this set RL/MRL value is confirmed by processing and analyzing seven replicates of laboratory fortified blanks (LFB) that are fortified with analyte at or below the set RL/MRL concentration. The LFB also include all method-specified dechlorination agents (e.g., ammonium chloride) and preservatives, which are included in typical sample preparation.

First, the results of the analytical run are used to determine the mean concentrations of the LFB and their standard deviations.

Second, the Half Range for the prediction interval of results (HRPIR) are calculated using the following equation:

$$HR_{PIR} = 3.963 \times S$$

Where:
S=standard deviation of the seven LFB concentration measurements; and
3.963 is the factor specific to seven replicates.

An upper and lower limit of the Prediction Interval of Result (PIR=Mean±$HR_{PIR}$) provides confirmation of the set RL/MRL if it meets two criteria: The Upper PIR Limit ($PIR_{UL}$) must be ≤150% recovery and The Lower PIR Limit ($PIR_{LL}$) must be ≥50% recovery for the RL/MRL to be confirmed. The calculations for PIR LL and $PIR_{LL}$ are as follows:

$$PIR_{UL} = \frac{\text{Mean} + HP_{PIR}}{\text{Fortified Concentration}} \times 100 \leq 150\%$$

$$PIR_{LL} = \frac{\text{Mean} - HP_{PIR}}{\text{Fortified Concentration}} \times 100 \geq 50\%$$

In step 230, samples from various sources of water are collected and analyzed using the above described method. For example, samples are collected in 250 mL polypropylene bottles. In some cases, the 250 mL bottles are pre-charged with approximately 50 mg of ammonium chloride.

In an example for the analysis of PFAS in tap water, the water tap is allowed to run freely until the water temperature has stabilized, and the flow is reduced to permit bottle filling without splashing. The bottle is filled to the neck, taking care not to flush out the ammonium chloride, if present. The bottle is then capped and agitated to dissolve the ammonium chloride, if present, and placed in a cooler with frozen gel packs.

In some cases, the samples received at the laboratory on the collection day are transported in coolers with frozen gel packs and their temperature is maintained between 1° C. and 10° C. for the first 48 hours.

In other cases, the samples that will not be received at the laboratory on the day of collection are maintained at a temperature range between approximately 1° C. to 6° C. until analysis is initiated at a receiving laboratory. Typically, a maximum holding time from collection to analysis is 14 days.

Samples are typically prepared for analysis by removing from refrigeration and allowing the samples to equilibrate to ambient temperature. In most cases, the samples are checked for dechlorination efficiency by testing with free chlorine strips to ensure that the free chlorine level is <0.1 mg/L. Samples, standards, and QCs are next loaded into 2 mL autosampler vials. In some cases, the samples and QCs are spiked with 10 µL of an internal standard as described supra.

The samples are then analyzed by injection alongside the standards and QCs into an LC/MS/MS with ESI using the conditions described supra.

After the initial calibration is confirmed valid with the QCS and CCV, analyzing field and QC samples is typically begun at the frequency outlined in Table 8 (supra). The instrument's MASS HUNTER software is used in the calibration procedure.

MASS HUNTER analytical software uses peak areas and the internal standard technique to calculate concentrations of the method analytes. Data may be fit with either a linear or quadratic regression with weighting if necessary. The calibration curve for PFOS and PFOA should be forced through the origin. The percent recovery calculation for CCV, LFB, QCS and LFM is performed using the following formula:

$$P = \frac{A - B}{T} \times 100\%$$

Where:

P=percent recovery;

A=measured concentration of analyte after spiking;

B=measured background concentration of analyte; and

T-true concentration of the spike.

Relative percent difference for the fortified matrix duplicate is calculated using the following formula:

$$RPD = \frac{|LMF - LFMD|}{\frac{LFM + LFMD}{2}} \times 100\%$$

Where:

RPD=relative percent difference;

LFM=measured concentration of analyte in the fortified sample; and

LFMD=measured concentration of analyte in the fortified sample duplicate.

Internal Standard Response Relative Percent Deviation (ISRPD) is calculated as follows:

$$ISRPD = \frac{IS \text{ Response in the Sample} - \text{Average } IS \text{ Response in the Initial Calibration}}{\text{Average } IS \text{ Response in the Initial Calibration}} \times 100$$

It should be appreciated that all combinations of the foregoing embodiments and additional embodiments discussed in greater detail herein (provided such embodiments are not mutually inconsistent) are contemplated as being part of the inventive subject matter disclosed herein. In particular, all combinations of claimed subject matter appearing at the end of this disclosure are contemplated as being part of the inventive subject matter disclosed herein.

Although the invention has been described by reference to specific examples, it should be understood that numerous changes may be made within the spirit and scope of the inventive concepts described. Accordingly, it is intended that the disclosure not be limited to the described examples, but that it have the full scope defined by the language of the following claims.

What is claimed is:

1. A method for facilitating detecting PFAS analytes in a sample comprising:
   injecting a volume of the sample into an LC/MS/MS system that is configured to detect one or more PFAS analytes of formula $C_nF_{(2n+1)}$—X within an unconcentrated sample;
   wherein:
   the LC/MS/MS includes ESI;
   n is 3, 4, 5, 6, 7, 8 or 9; and
   —X is —$SO_3H$, —$CO_2H$, —$SO_3^-$, or —$CO_2^-$;
   subjecting the injected volume of the sample to ESI conditions that include a sheath gas flow of approximately 8 L/min to approximately 12 L/min; and
   detecting one or more PFAS analytes within the sample.

2. The method of claim 1 further comprising determining:
   i) a concentration of the at least one PFAS analyte within the sample that is at least approximately 0.010 µg/L; and/or
   ii) an amount of the at least one PFAS analyte within the injected volume of the sample that is at least approximately 7.5×107 µg.

3. The method of claim 1, wherein the ESI conditions further comprise a sheath gas heater setting of approximately 250° C. to approximately 400° C.

4. The method of claim 1, wherein the ESI conditions further comprise a probe gas temperature of approximately 120° C. to approximately 180° C.

5. The method of claim 1, wherein the ESI conditions further comprise a gas flow setting of between approximately 11 L/min to approximately 20 L/min.

6. The method of claim 1, wherein the ESI conditions further comprise a capillary voltage setting of between approximately 1500 V to approximately 4500 V.

7. The method of claim 2, wherein the one or more PFAS analytes of formula $C_nF_{(2n+1)}$—X are chosen from: PFBA, PFBS, PFDA, PFHpA, PFHpS, PFHxA, PFHxS, PFNA, PFPeS, PFOA, and PFOS.

8. The method of claim 1, wherein the PFAS analytes of formula $C_nF_{(2n+1)}$—X are PFOA or PFOS.

9. The method of claim 8, wherein one PFAS analyte of formula $C_nF_{(2n+1)}$—X is PFOA.

10. The method of claim 8, wherein one PFAS analyte of formula $C_nF_{(2n+1)}$—X is PFOS.

11. A PFAS analyte detection system comprising:
an LC/MS/MS system operable utilizing ESI and configured to:
receive an injected volume of a sample containing one or more PFAS analytes of formula $C_nF_{(2n+1)}$—X;
wherein:
n is 3, 4, 5, 6, 7, 8 or 9; and
—X is —$SO_3H$, —$CO_2H$, —$SO_3^-$, or —$CO_2^-$;
subject the injected volume of the sample to ESI conditions that include a probe gas temperature of approximately 120° C. to approximately 180° C.; and
detect one or more PFAS analytes within the sample.

12. The system of claim 11, wherein the LC/MS/MS system is configured to determine:
i) a concentration of the at least one PFAS analyte within the sample that is at least approximately 0.010 μg/L; and/or
ii) an amount of the at least one PFAS analyte within the injected volume of the sample that is at least approximately $7.5 \times 10^{-7}$ μg.

13. The system of claim 11, wherein the ESI conditions further comprise a sheath gas heater setting of approximately 250° C. to approximately 400° C.

14. The system of claim 11, wherein the ESI conditions further comprise a sheath gas flow of approximately 8 L/min. to approximately 12 L/min.

15. The system of claim 11, wherein the ESI conditions further comprise a gas flow setting of between approximately 11 L/min to approximately 20 L/min.

16. The system of claim 11, wherein the ESI conditions further comprise a capillary voltage setting of approximately 1500 V to approximately 4500 V.

17. The system of claim 11, wherein a detectable amount of PFAS analyte in a single received injection of sample is at least approximately $1.5 \times 10^{-7}$ μg.

18. The system of claim 11, wherein the one or more PFAS analytes of formula $C_nF_{(2n+1)}$—X are chosen from: PFBA, PFBS, PFDA, PFHpA, PFHpS, PFHxA, PFHxS, PFNA, PFPeS, PFOA, and PFOS.

19. The system of claim 11, wherein the PFAS analytes of formula $C_nF_{(2n+1)}$—X are PFOA or PFOS.

20. The system of claim 19, wherein one PFAS of formula $C_nF_{(2n+1)}$—X is PFOA.

21. The system of claim 19, wherein one PFAS of formula $C_nF_{(2n+1)}$—X is PFOS.

22. A method for facilitating the detection of PFAS analytes in a sample comprising:
obtaining a sample containing one or more PFAS analytes of formula $C_nF_{(2n+1)}$—X;
wherein:
n is 3, 4, 5, 6, 7, 8 or 9; and
—X is —$SO_3H$, —$CO_2H$, —$SO_3$, or —$CO_2$
receiving data representative of test results of an analysis detecting at least one of the one or more PFAS analytes of formula $C_nF_{(2n+1)}$—X within at least a portion of the sample, the test results comprising one or both: i) the concentration of the at least one PFAS analyte in the sample; and ii) the amount within an injected volume of the sample of the at least one PFAS analyte into an LC/MS/MS system;
wherein:
i) the concentration of the at least one PFAS analyte within the sample is between approximately 0.0020 μg/L and approximately 0.25 μg/L; and/or
ii) the amount of the at least one PFAS analyte within the injected volume of the sample is between approximately $1.5 \times 10^{-7}$ μg and approximately $1.9 \times 10^{-5}$ μg;
wherein the analysis comprised the following steps a) and b):
a) injecting a volume of the sample into the LC/MS/MS system with ESI that is configured to detect the at least one PFAS analyte; and
b) subjecting the injected volume of the sample to ESI conditions that include a sheath gas flow of approximately 8 L/min to approximately 12 L/min.

* * * * *